(12) United States Patent
Reardon et al.

(10) Patent No.: US 9,796,998 B2
(45) Date of Patent: Oct. 24, 2017

(54) OXYGENASE-BASED BIOSENSING SYSTEMS FOR MEASUREMENT OF HALOGENATED ALKENE CONCENTRATIONS

(71) Applicant: Colorado State University Research Foundation, Fort Collins, CO (US)

(72) Inventors: Kenneth F. Reardon, Fort Collins, CO (US); Brian C. Heinze, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 0 days.

(21) Appl. No.: 14/348,426

(22) PCT Filed: Oct. 1, 2012

(86) PCT No.: PCT/US2012/058331
§ 371 (c)(1),
(2) Date: Mar. 28, 2014

(87) PCT Pub. No.: WO2013/049831
PCT Pub. Date: Apr. 4, 2013

(65) Prior Publication Data
US 2014/0234882 A1   Aug. 21, 2014
US 2017/0269001 A9   Sep. 21, 2017

Related U.S. Application Data

(63) Continuation-in-part of application No. 13/562,592, filed on Jul. 31, 2012, now Pat. No. 9,493,806, which is a continuation-in-part of application No. 12/100,308, filed on Apr. 9, 2008, now Pat. No. 9,493,805.

(60) Provisional application No. 61/541,421, filed on Sep. 30, 2011, provisional application No. 60/922,496, filed on Apr. 9, 2007.

(51) Int. Cl.
| | |
|---|---|
| *C12Q 1/48* | (2006.01) |
| *C12Q 1/32* | (2006.01) |
| *C12N 9/02* | (2006.01) |
| *C12N 9/10* | (2006.01) |
| *G01N 21/77* | (2006.01) |
| *C12Q 1/26* | (2006.01) |
| *C12Q 1/34* | (2006.01) |
| *G01N 21/64* | (2006.01) |
| *C12M 1/34* | (2006.01) |

(52) U.S. Cl.
CPC ............. *C12Q 1/48* (2013.01); *C12N 9/0069* (2013.01); *C12N 9/0071* (2013.01); *C12N 9/1088* (2013.01); *C12Q 1/26* (2013.01); *C12Q 1/34* (2013.01); *G01N 21/6428* (2013.01); *C12Y 113/00* (2013.01); *C12Y 114/00* (2013.01)

(58) Field of Classification Search
None
See application file for complete search history.

(56) References Cited

U.S. PATENT DOCUMENTS

| | | |
|---|---|---|
| 4,739,380 A | 4/1988 | Lauks et al. |
| 4,832,034 A | 5/1989 | Pizziconi et al. |
| 4,848,906 A | 7/1989 | Layton |
| 4,900,423 A | 2/1990 | Iida et al. |
| 5,140,609 A | 8/1992 | Jensen et al. |
| 5,141,312 A * | 8/1992 | Thompson ............... G01J 1/04 250/227.11 |
| 5,152,758 A | 10/1992 | Kaetsu et al. |
| 5,156,810 A | 10/1992 | Ribi |
| 5,177,012 A | 1/1993 | Kim et al. |
| 5,250,439 A | 10/1993 | Musho et al. |
| 5,340,722 A * | 8/1994 | Wolfbeis ................ C12Q 1/005 435/14 |
| 5,462,879 A | 10/1995 | Bentsen |
| 5,508,193 A | 4/1996 | Mandelbaum et al. |
| 5,541,057 A | 7/1996 | Bogart et al. |
| 5,543,317 A | 8/1996 | Shields et al. |
| 5,580,527 A * | 12/1996 | Bell ...................... C12Q 1/005 435/14 |
| 5,629,214 A | 5/1997 | Crosby |
| 5,698,083 A | 12/1997 | Glass |
| 5,798,030 A | 8/1998 | Raguse et al. |
| 5,837,196 A | 11/1998 | Pinkel et al. |
| 5,837,454 A | 11/1998 | Cozzette et al. |
| 5,853,669 A * | 12/1998 | Wolfbeis ............... G01N 31/221 422/408 |
| 5,866,321 A | 2/1999 | Matsue et al. |
| 5,972,199 A | 10/1999 | Heller et al. |
| 5,972,638 A | 10/1999 | Burlage et al. |

(Continued)

FOREIGN PATENT DOCUMENTS

| | | |
|---|---|---|
| EP | 277699 A2 | 10/1988 |
| EP | 1078248 B1 | 2/2001 |

(Continued)

OTHER PUBLICATIONS

Carswell, Richard; Khoie, Abdol R. "Optical Oxygen Sensor Based on RuDPP Fluorescence Quenching", Proc. SPIE 2705, Fluorescence Detection IV, Mar. 25, 1996, pp. 22-30 (doi:10.1117/12.236194).*

(Continued)

*Primary Examiner* — Chris R Tate
*Assistant Examiner* — Aaron J Kosar
(74) *Attorney, Agent, or Firm* — Faegre Baker Daniels LLP

(57) ABSTRACT

A biosensing system that measures the concentration of halogenated alkenes is disclosed.

14 Claims, 11 Drawing Sheets

(56) References Cited

U.S. PATENT DOCUMENTS

| | | | |
|---|---|---|---|
| 6,022,748 | A | 2/2000 | Charych et al. |
| 6,060,327 | A | 5/2000 | Keen |
| 6,100,080 | A | 8/2000 | Johansen |
| 6,136,979 | A | 10/2000 | Hudlicky et al. |
| 6,159,681 | A | 12/2000 | Zebala |
| 6,265,201 | B1 | 7/2001 | Wackett et al. |
| 6,271,015 | B1 | 8/2001 | Gilula |
| 6,284,522 | B1 | 9/2001 | Wackett et al. |
| 6,291,200 | B1 | 9/2001 | LeJeune et al. |
| 6,344,360 | B1 | 2/2002 | Colvin et al. |
| 6,369,299 | B1 | 4/2002 | Sadowsky et al. |
| 6,437,345 | B1 | 8/2002 | Bruno-Raimondi et al. |
| 6,576,449 | B2 | 6/2003 | Clark et al. |
| 6,592,746 | B1 | 7/2003 | Schmid-Schoenbein et al. |
| 6,766,183 | B2 | 7/2004 | Walsh et al. |
| 6,825,001 | B2 | 11/2004 | Wackett et al. |
| 6,927,246 | B2 | 8/2005 | Noronha et al. |
| 7,381,538 | B2 | 6/2008 | Reardon et al. |
| 7,595,181 | B2 | 9/2009 | Gruning et al. |
| 7,709,221 | B2 | 5/2010 | Rose et al. |
| 7,709,249 | B2 | 5/2010 | Bedingham et al. |
| 7,955,483 | B2 | 6/2011 | Gu et al. |
| 8,309,328 | B1 | 11/2012 | Dhawan et al. |
| 8,323,956 | B2 | 12/2012 | Reardon et al. |
| 8,622,900 | B2 | 1/2014 | Jain et al. |
| 8,622,901 | B2 | 1/2014 | Jain et al. |
| 9,493,805 | B2 | 11/2016 | Reardon |
| 9,493,806 | B2 | 11/2016 | Reardon |
| 9,499,853 | B2 | 11/2016 | Reardon |
| 2002/0168733 | A1 | 11/2002 | Clark et al. |
| 2003/0207345 | A1 | 11/2003 | Arnold |
| 2004/0265811 | A1 | 12/2004 | Reardon et al. |
| 2005/0084921 | A1 | 4/2005 | Cranley et al. |
| 2005/0221276 | A1 | 10/2005 | Rozakis et al. |
| 2006/0275855 | A1 | 12/2006 | Blackburn et al. |
| 2009/0026092 | A1 | 1/2009 | Reardon et al. |
| 2009/0078886 | A1 | 3/2009 | Schutzmann et al. |
| 2009/0221014 | A1 | 9/2009 | Reardon et al. |
| 2010/0116691 | A1 | 5/2010 | Papadimitrakopoulos |
| 2013/0065224 | A1 | 3/2013 | Lu et al. |
| 2014/0154724 | A1* | 6/2014 | Reardon ............ 435/25 |
| 2014/0234882 | A1 | 8/2014 | Reardon et al. |
| 2014/0235501 | A1 | 8/2014 | Reardon |
| 2015/0232913 | A1 | 8/2015 | Reardon et al. |

FOREIGN PATENT DOCUMENTS

| | | |
|---|---|---|
| EP | 1369687 A1 | 12/2003 |
| WO | WO 93/25892 | 12/1993 |
| WO | 9958963 A1 | 11/1999 |
| WO | 03025627 A9 | 3/2003 |
| WO | 2004060297 A2 | 7/2004 |
| WO | 2009126841 A1 | 10/2009 |

OTHER PUBLICATIONS

Hollman, F. et al, Angew. Chem Int. Ed., 2001, 40(1), 169-171 (DOI: 10.1002/1521-3773(20010105)40:1<169::AID-ANIE169>3.0.CO;2-T).*

Zhong, Z. and Reardon, K.F. "Fiber Optic Enzymatic Biosensors and Biosensor Arrays for Measurement of Chlorinated Ethenes" Dissertation, CSU Dept of Chem and Biol. Eng., Spring 2011 (Aug. 21, 2011), pp. i-ix and 1-148.*

Lee, J et al "Proteome Changes after Metabolic Engineering to Enhance Aerobic Mineralization of cis-1,2-Dichloroethylene" J. Proteome Res., 2006,5(6),pp. 1388-1397.*

Rui, L; Kwon, Y.M.; Reardon, K.F.; Wood, T.K. "Metabolic pathway engineering to enhance aerobic degradation of chlorinated ethenes and to reduce their toxicity by cloning a novel glutathione S-transferase, an evolved toluene o-monooxygenase, and gamma-glutamylcysteine synthetase" Environ. Microbiol.,2004,6(5), pp. 491-500.*

Godfrey, Larry "Choosing the Detector for your Unique Light Sensing Application" EG&G Optoelectronics Data Sheet, 1997, 6 pages.*

Adachi, K., et al; Purification and properties of homogentisate oxygenase from Pseudomonas fluorescens. Biochim. Biophys. Acta 118 (1966) 88-97.

Aldridge, W.N.; Serum esterases. I. Two types of esterase (A and B) hydrolysing p-nitrophenyl acetate, propionate and butyrate and a method for their determination. Biochem. J. 53 (1953) 110-117.

Amitai, G. et al.; Enhanced stereoselective hydrolysis of toxic organophosphates by directly evolved variants of mammalian serum paraoxonase; FEBS Journal 273 (2006) pp. 1906-1919.

Augusteyn, R.C., et al; On the homology of the active-site peptides of liver Carboxylesterases. Biochim. Biophys. Acta 171 (1969) 128-137.

Augustinsson, K.-B. and Heimburger, G. Enzymatic hydrolysis of organophosphorus compounds. I. Occurrence of enzymes hydrolysing dimethyl-amido-ethoxy-phosphoryl cyanide (Tabun). Acta Chem. Scand. 8 (1954) 753-761.

Bertoni, G., et al; "Cloning of the Genes for and Characterization of the Early Stages of Toluene and o-Xylene Catabolism in Pseudomonas stutzeri OX1," Applied and Environmental Microbiology, 1996, 62(10): pp. 3704-3711.

Bertoni, G., et al; "Analysis of the Gene Cluster Encoding Toluene/o-Xylene Monoxygenase from Pseudomonas stutzeri OX1," Applied and Environmental Microbiology, 1998. 64(10): pp. 3626-3632.

Buchinger, P.J. et al.; Characteristics of Microbial Assay for the Detection of Halogenated Hydrocarbons Using Cells of an Actinomycete-like Organism as a Biological Component; Acta Biotechnol. 17 (1997) 2, 123-130.

Byrne, A.M., et al; "Sequence Analysis of the Gene Cluster Encoding Toluene-3-monooxygenase from Pseudomonas pickettii PK01," Gene, 1995. 154: pp. 65-70.

Cardini, G. & Jurtshuk, P. The enzymatic hydroxylation of n-octane by *Corynebacterium* sp. strain 7E1C. J. Biol. Chem. 245 (1970) 2789-2796.

Cardy, D.L.N., V. Laidler, G.P.C. Salmond, and J.C. Murrell, "Molecular Analysis of the Methane Monooxygenase (MMO) Gene Cluster of Methylosinus trichosporium OB3b," Molecular Microbiology, 1991. 5(2): pp. 335-342.

Chang, K. H., et al; Isolation and characterization of the three polypeptide components of 4-chlorobenzoate dehalogenase from *Pseudomonas* sp. strain CBS-3. Biochemistry 31 (1992) 5605-5610.

Chopra, I. J. & Teco, G. N. C. Characteristics of inner ring (3 or 5) monodeiodination of 3,5-diiodothyronine in rat liver: evidence suggesting marked similarities of inner and outer ring deiodinases for iodothyronines. Endocrinology 110 (1982) 89-97.

Colby, J. et al; The soluble methane mono-oxygenase of Methylococcus capsulatus (Bath). Its ability to oxygenate n-alkanes, n-alkenes, ethers, and alicyclic, aromatic and heterocyclic compounds. Biochem. J. 165 (1977) 395-402.

Crooks, G. P. & Copley, S. D.; Purification and characterization of 4-chlorobenzoyl CoA dehalogenase from *Arthrobacter* sp. strain 4-CB1. Biochemistry, 33 (1994) 11645-11649.

de Souza, M. L. et al; Cloning, characterization, and expression of a gene region from *Pseudomonas* sp. strain ADP involved in the dechlorination of atrazine. Appl. Environ. Microbiol. 61 (1995) 3373-3378.

de Souza, M. L., et al; Atrazine chlorohydrolase from *Pseudomonas* sp. strain ADP: gene sequence, enzyme purification, and protein characterization. J. Bacteriol. 178 (1996) 4894-4900.

Dodgson, K.S., et al; Studies on sulphatases. 13. The hydrolysis of substituted phenyl sulphates by the arylsulphatase of Alcaligenes metacaligenes. Biochem. J. 64 (1956) 216-221.

Ensley, B.D. & Gibson, D.T. Naphthalene dioxygenase: purification and properties of a terminal oxygenase component. J. Bacteriol. 155 (1983) 505-511.

Fetzner, S., et al; Degradation of 2-chlorobenzoate by Pseudomonas cepacia 2CBS. Biol. Chem. Hoppe-Seyler 370 (1989) 1173-1182.

Fox, B.G., et al., "Methane Monooxygenase from Methylosinus trichosporium OB3b," Journal of Biological Chemistry, 1989. 264(17): pp. 10023-10033.

(56) References Cited

OTHER PUBLICATIONS

Fujisawa, H. & Hayaishi, O.; Protocatechuate 3,4-dioxygenase. I. Crystallization and characterization. J. Biol. Chem. 243 (1968) 2673-2681.
Goldman, P. & Milne, G. W. A.; Carbon-fluorine bond cleavage. II. Studies on the mechanism of the defluorination of fluoroacetate. J. Biol. Chem. 241 (1966) 5557-5559.
Goldman, P., et al.; Carbon-halogen bond cleavage. 3. Studies on bacterial halidohydrolases. J. Biol. Chem. 243 (1968) 428-434.
Goldman, P.; the enzymatic cleavage of the carbon-fluorine bond in fluoroacetate. J. Biol. Chem. 240 (1965) 3434-3438.
Goswami A., et al.; Inhibition by coumadin anticoagulants of enzymatic outer ring monodeiodination of iodothyronines. Biochem. Biophys. Res. Commun. 104 (1982) 1231-1238.
Hayaishi, O. & Sutton, W.B. Enzymatic oxygen fixation into acetate concomitant with the enzymatic decarboxylation of L-lactate. J. Am. Chem. Soc. 79 (1957) 4809-4810.
Heppel, L. A. & Porterfield, V. T. Enzymatic dehalogenation of certain brominated and chlorinated compounds. *J. Biol. Chem.* 176 (1948) 763-769.
Hosokawa, K. & Stanier, R.Y. Crystallization and properties of p-hydroxybenzoate hydroxylase from Pseudomonas putida. J. Biol. Chem. 241 (1966) 2453-2460.
Junker, F., et al; Dioxygenation and spontaneous deamination of 2-aminobenzene sulphonic acid in *Alcaligenes* sp. strain O-1 with subsequent meta ring cleavage and spontaneous desulphonation to 2-hydroxymuconic acid. Biochem. J. 300 (1994) 429-436.
Keuning, S., Janssen, D. B. & Witholt, B.; Purification and characterization of hydrolytic haloalkane dehalogenase from Xanthobacter autotrophicus GJ10; J. Bacteriol. 163 (1985) 635-639.
Kohler-Staub, D. & Leisinger, T.; Dichloromethane dehalogenase of *Hyphomicrobium* sp. strain DM2. J. Bacteriol. 162 (1985) 676-681.
Kumagai, H., et al; S-Carboxymethylcysteine synthase from *Escherichia coli*. Agric. Biol. Chem. 53 (1989) 2481-2487.
Lipke, H. & Kearns, C. W.; DDT dechlorinase. I. Isolation, chemical properties, and spectrophotometric assay. J. Biol. Chem. 234 (1959) 2123-2128.
Lipke, H. & Kearns, C. W.; DDT dechlorinase. II. Substrate and cofactor specificity. J. Biol. Chem. 234 (1959) 2129-2132.
McClay, K., B.G. Fox, and R.J. Steffan, "Chloroform Mineralization by Toluene-Oxidizing Bacteria," Applied and Environmental Microbiology, 1996. 62(8): pp. 2716-2722.
Moorefield, H. H. Purification of DDT-dehydrochlorinase from resistant houseflies. Contr. Boyce Thompson Inst. 18 (1956) 303-310.
Moriguchi, M., et al.; Dehalogenation and deamination of 1-2-amino-4-chloro-4-pentenoic acid by Proteus mirabilis. Agric. Biol. Chem. 51 (1987) 3295.
Motosugi, M., et al.; Preparation and properties of 2-halo acid dehalogenase from Pseudomonas putida. Agric. Biol. Chem. 46 (1982) 837-838.
Mulchandani, A. et al.; Biosensor for Direct Determination of Organophosphate Nerve Agents Using Recombatant *Escherichia coli* with Surface-Expressed Organophosphorus Hydrolase.—2. Fiber-Optic Microbial Bionsenor; ., Analytical Chemistry 1998 70 (23), 5042-5046.
Muller, C. et al.; Multicomponent fiberoptical biosensor for use in hemodialysis monitoring; SPIE Biomedical Fiber Optic Instrumentation; vol. 2131; pp. 555-562 (Jul. 1994).
Muller, R., et al.; Incorporation of [18O] water into 4-hydroxybenzoic acid in the reaction of 4-chlorobenzoate dehalogenase from *Pseudomonas* sp. CBS 3. Biochem. Biophys. Res. Commun. 124 (1984) 178-182.
Nagasawa, T.,et al.; Physiological comparison of D-cysteine desulfhydrase of *Escherichia coli* with 3-chloro-D-alanine dehydrochlorinase of Pseudomonas putida CR 1-1. Arch. Microbiol. 149 (1988) 413-416.
Nakagawa, H. and Takeda, Y. Phenol hydroxylase. Biochim. Biophys. Acta 62 (1962) 423-426.

Nordlund, I., et al, "Complete nucleotide sequence and polypeptide analysis of multicomponent phenol hydroxylase from Pseudomonas strain CF600," Journal of Bacteriology, 1990. 172: pp. 6826-6833.
PCT/US2002/017407 International Search Report; mailed Sep. 24, 2003; 2 pages.
PCT/US2009/040121, International Search Report & Written Opinion mailed Jul. 14, 2009, 7 Pages.
Pikus, J.D., et al; "Recombinant Toluene-4-Monoxygenase: Catalytic and Mossbauer Studies of the Purified Diiron and Rieski Components of a Four-Protein Complex," Biochemistry, 1996. 35: pp. 9106-9119.
Ramanathan, M. & Simonian, A.L.; Array biosensor based on enzyme kinetics monitoring by fluorescence spectroscopy: Application for neurotoxins detection; Biosensors and Bioelectronics 23 (2007) pp. 3001-3007.
Renganathan, V. Possible involvement of toluene-2,3-dioxygenase in defluorination of 3-fluoro-substituted benzenes by toluene-degrading *Pseudomonas* sp. strain T-12. Appl. Exp. Microbiol. 55 (1989) 330-334.
Rosenzwieg, A.C., et al. "Geometry of the Soluble Methane Monoxygenase Catalytic Diiron Center in Two Oxidation States," Chemistry and Biology, 1995. 2(6): pp. 409-418.
Schenk, T.,et al.; Enzymatic dehalogenation of pentachlorophenol by extracts from *Arthrobacter* sp. strain ATCC 33790. J. Bacteriol. 171 (1989) 5487-5491.
Scholtz, R., et al.; Characterization of 1-chlorohexane halidohydrolase, a dehalogenase of wide substrate range from an *Arthrobacter* sp. J. Bacteriol. 169 (1987) 5016-5021.
Simonian, AL, et al.; FET-Based Biosensors for The Direct Detection of Organophosphate Neurotoxins; Electroanalysis 2004; 16, No. 22; pp. 1896-1906.
Smallridge, R. C., et al. "3',5'-Diiodothyronine to 3'-monoiodothyronine conversion in the fed and fasted rat: enzyme characteristics and evidence for two distinct 5'-deiodinases" Endocrinology 108 (1981) 2336-2345.
Stainthorpe, A.C., et al., "The Methane Monooxygenase Gene Cluster of Methylococcus capsulatus (Bath)," Gene, 1990. 91: pp. 27-34.
Suzuki, K., Takemori, S. and Katagiri, M. Mechanism of the salicylate hydroxylase reaction. IV. Fluorimetric analysis of the complex formation. Biochim. Biophys. Acta 191 (1969) 77-85.
Yamada, H., et al; Synthesis of D-cysteine from 3-chloro-D-alanine and hydrogen sulfide by 3-chloro-D-alanine hydrogen chloride-lyase (deaminating) of Pseudomonas putida. Biochem. Biophys. Res. Commun. 100 (1981) 1104-1110.
Yen, K.-M., "Construction of Cloning Cartridges for Development of Expression Vectors in Gram-Negative Bacteria," J. Bacteriol., 1991. 173(17): pp. 5328-5335.
Yokota, T., et al.; Purification and properties of haloalkane dehalogenase from *Corynebacterium* sp. strain m15-3. J. Bacteriol. 169 (1987) 4049-4054.
Ziegler, D.M. and Pettit, F.H. Microsomal oxidases. I. The isolation and dialkylarylamine oxygenase activity of pork liver microsomes. Biochemistry 5 (1966) 2932-2938.
Conzuelo, F. et al., An Integrated amperometric biosensor for the determination of lactose in milk and dairy products, J. Agric. Food Chern., Jun. 23, 2010, pp. 7141-7148.
Jenkins, D.M. et al. Adaptation of a manometric biosensor to measure glucose and lactose, Biosensors Bioelectronics, Jan. 31, 2003, pp. 101-107.
Plata, M.R. et al., State-of-the-art of (bio)chemical sensor developments in analytical spanish groups , Sensors, Mar. 24, 2010, pp. 2511-2576.
PCT/US11/61956 International Search Report and Written Opinion mailed Jun. 14, 2012, 10 pages.
PCT/US12/49384 International Search Report and Written Opinion mailed Feb. 20, 2012, 11 pages.
PCT/US02/17407, International Preliminary Examination Report, Mar. 5, 2005, 4 pages.
U.S. Appl. No. 10/478,822.
U.S. Appl. No. 12/100,308.
U.S. Appl. No. 12/358,140.

(56) References Cited

OTHER PUBLICATIONS

Mills, A. et al., Reversible, fluorescence-based optical sensor for hydrogen peroxide. Analyst 132 2007) 566-571.
Posch, H.E. & Wolfbeis. O.S., Optical sensor for hydrogen peroxide. Microchimica Acta 97 (1989) 41-50.
Rajendran, V., Lrudayaraj, J. Detection of glucose, galactose, and lactose in milk with a microdialysis-coupled flow injection amperometric sensor. J Dairy Sci. 85 (2002) 1357-61.
Pilloton, R et al., Lactose Determination in Raw Milk with a Two-Enzyme Based Electrochemical Sensor. Analytical Letters. 20 (1987) 1803-1814.
Tkác J, et al., Novel glucose non-interference biosensor for lactose detection based on galactose oxidase-peroxidase with and without co-immobilised beta-galactosidase. Analyst. 125 (2000) 1285-9.
Wichmann, R. & Vasic-Racki. D.; Cofactor Regeneration at the Lab Scale. Adv Biochem Engin/Biotechnol 92 (2005) 225-260.
Zhao, H. & van der Donk, W.A.. Regeneration of cofactors for use in biocatalysis. Current Opinion in Biotechnology. 14 (2003) 583-589.
Woodyer, R.D. et al. (2005) Regeneration of cofactors for enzyme biocatalysis. Enzyme Technology, 85-103.
Johannes, T.W. et al. (2005). Directed evolution of a thermostable phosphite dehydrogenase for NAD(P)H regeneration. Applied and Environmental Microbiology, 71(10), 5728-5734. doi:10.1128/AEM.71.10.5728-5734.2005.
Snaked, Z. & Whitesides, G.M., Enzyme-catalyzed organic synthesis: NADH regeneration by using formate dehydrogenase. J. Am. Chem. Soc. 102 (1980) 7104-7105.
Berríos-Rivera, .S.J. et al. Metabolic engineering of *Escherichia coli*: increase of NADH availability by overexpressing an NAD(+)-dependent formate dehydrogenase. Metab Eng. 4 (2002) 217-29.
Zhong et al., Fiber optic monooxygenase biosensor for toluene concentration measurement in aqueous samples, Biosensors and Bioelectronics, Jan. 15, 2011, vol. 26, Iss. 5, pp. 2407-2412.
PCT/US2012/058331 International Search Report & Written Opinion mailed Mar. 29, 2013, 11 pages.
Mars et al. "Effect of Trichloreothylene on Competitive Behavior of Toluene-Degrading Bacteria," Applied and Environmental Microbiology, 1998, vol. 64 (1), pp. 208-215.
Neujahr, Halina, "Determination of Phenol and Catechol Concentrations with Oxygen Probes Coated with Immobilized Enzymes or Immobilized Cells," Applied Biochemistry and Biotechnology, 1982, vol. 7, pp. 107-111.
Rui et al. "Metabolic pathway engineering to enhance aerobic degradation of chlorinated ethenes and to reduce their toxicity by cloning a novel glutathione S-transferase, an evolved toluene o-monooxygenase, and y-glutamylcysteine synthetase," Environmental Microbiology, 2004, 6(5), pp. 491-500.
Stokes et al. "An optical oxygen sensor and reaction vessel for high-pressure applications," Limnol. Ocearnogr., 1999, vol. 44(1 ):189-195.
Sundari et al. "Retention of enzyme activity following freeze-drying the mycelium of ectomycorrhizal isolates: part II. Enzymes acting upon carbon compounds" World Journal of Microbiology and Biotechnology, 2000, vol. 16, pp. 865-868.
U.S. Appl. No. 12/100,308, Office Action mailed Apr. 6, 2015; 9 pages.
U.S. Appl. No. 14/236,531, Office Action mailed Aug. 1, 2014, 16 pages.
U.S. Appl. No. 14/236,531, Response to Office Action filed Jan. 31, 2015, 17 pages.
U.S. Appl. No. 14/236,531, Notice of Allowance dated Mar. 16, 2015, 7 pages.
U.S. Appl. No. 14/236,531, Notice of Allowance dated Jun. 26, 2015, 7 pages.
Zakhari, S. "Overview: How Is Alcohol Metabolized by the Body?" NIAAA Publications, Dec. 2006, vol. 29, No. 4, 12 pages.
Mars, et al., "Effect of Trichloroethylene on the Competitive Behavior of Toluene-Degrading Bacteria," Applied and Environmental Microbiology, vol. 64, No. 1 (Jan. 1998), pp. 208-215.
Mills, "Optical Oxygen Sensors, Utilising the Luminescence of Platinum Metals Complexes," Platinum Metals Review, vol. 41, Issue 3 (1997) pp. 115-127.
van Beilen, et al., "Practical issues in the application of oxygenases," TRENDS in Biotechnology, vol. 21, No. 4, Apr. 2003, pp. 170-177.
Al-Raweshidy, H.S., et al. Electro-optic correlation in a spread specrum multiplexing system for fibre optic interferometers, Optics Communications 81 dated Feb. 15, 1991, pp. 171-174.
U.S. Appl. No. 13/562,592, Non-Final Rejection dated Oct. 8, 2015, 20 pages.
Chudobova, Ivana et al, "Fibre optic biosensor for the determination of D-glucose based on absorption changes of immobilized glucose oxidase," Analytica Chimica Acta, Issue 319 (1996) pp. 103-110.
Ferri, et al., "Review of Glucose Oxidases and Glucose Dehydrogenases: A Bird's Eye View of Glucose Sensing Enzymes," Journal of Diabetes Science and Technology, vol. 5, Issue 5 (dated Sep. 2011), pp. 1068-1076.
Issue Notification dated May 14, 2008, for U.S. Appl. No. 10/478,822, 1 page.
Lipson, D. et al., Multifiber, Multiwavelength, Fiber Optic Flourescence Spectrophotometer, IEEE Trans. Biomed. Eng. vol. 39, No. 9 dated Sep. 1992, pp. 886-892.
Moreno-Bondi, Maria C., et al., Oxygen Optrode for Use in a Fiber-Optic Glucose Biosensor, Analytical Chemistry, vol. 62, No. 21 (dated Nov. 1, 1990), pp. 2377-2380.
Notice of Allowance dated Jan. 13, 2012, for U.S. Appl. No. 12/358,140, 7 pages.
Notice of Allowance dated Feb. 13, 2008, for U.S. Appl. No. 10/478,822, 3 pages.
Office Action issued in U.S. Appl. No. 14/348,426, dated Apr. 2, 2015, 19 pages.
Office Action dated Apr. 1, 2011, for U.S. Appl. No. 12/358,140, 8 pages.
Office Action dated Oct. 28, 2011, for U.S. Appl. No. 12/358,140, 9 pages.
Office Action dated Oct. 31, 2007, for U.S. Appl. No. 10/478,822, 6 pages.
Office Action dated May 17, 2007, for U.S. Appl. No. 10/478,822, 13 pages.
Peter, J. (1997). "Characteristics of a Microbial Assay for the Detection of Halogenated Hydrocarbons Using Cells of an Actinomycete-like Organism as a Biological Component." Acta Biotechnol. 17:(2). 123-130.
Response to Office Action dated Aug. 1, 2011, for U.S. Appl. No. 12/358,140, 15 pages.
Response to Office Action dated Dec. 28, 2007, for U.S. Appl. No. 10/478,822, 10 pages.
Response to Office Action dated Dec. 28, 2011, for U.S. Appl. No. 12/358,140, 27 pages.
Response to Office Action dated Aug. 17, 2007, for U.S. Appl. No. 10/478,822, 79 pages.
Response to Restriction Requirement dated Feb. 12, 2007, for U.S. Appl. No. 10/478,822, 6 pages.
Schaffar, Bernhard P.H., et al., "A Fast Responding Fibre Optic Glucose Biosensor Based on an Oxygen Optrode," Biosensors & Bioelectronics, Issue 5 (1990), pp. 137-148.
Steiner, Mark-Steven, et al., "Optical methods for sensing glucose," Chemical Society Reviews, Issue 9 (Sep. 1, 2011), pp. 4805-4839.
Trettnak, Wolfgang, et al., "A Fiberoptic Cholesterol Biosensor with an Oxygen Optrode as the Transducer," Analytical Biochemistry, Issue 184 (1990) pp. 124-127.
Trettnak, Wolfgang, et al., "Fibre Optic Glucose Biosensor With an Oxygen Optrode as the Transducer," Analyst, vol. 113 (Oct. 1988) pp. 1519-1523.
Trettnak, Wolfgang, et al., "Fibre-Optic Glucose Sensor with a pH Optrode as the Transducer," Biosensors, Issue 4 (1988), pp. 15-26.
Vilker, et al., "Challenges in Capturing Oxygenase Activity in Vitro," Journal of the American Oil Chemists' Society, vol. 76, No. 11 (1999), pp. 1283-1289.

(56) References Cited

OTHER PUBLICATIONS

Wilson, et al., "Glucose oxidase: an ideal enzyme," Biosensors & Bioelectronics, vol. 7 (1992), pp. 165-185.
Borisov, SM and Wolfbeis, OS "Optical Biosensors", Chemical Reviews, 2008, vol. 108, pp. 423-461.

* cited by examiner

OXYGENASE-BASED BIOSENSING SYSTEMS FOR MEASUREMENT OF HALOGENATED ALKENE CONCENTRATIONS

RELATED APPLICATIONS

This application is a national phase entry under 35 U.S.C. §371 of PCT/US12/58331 filed Oct. 1, 2012, which claims priority under 35 U.S.C. §119(e) to U.S. Provisional Patent Application No. 61/541,421 filed on Sep. 30, 2011, and which is a continuation-in-part application of U.S. patent application Ser. No. 13/562,592 filed on Jul. 31, 2012, which is a continuation-in-part application of U.S. patent application Ser. No. 12/100,308, filed Apr. 9, 2008, which claims priority to U.S. Provisional Patent Application Ser. No. 60/922,496, filed Apr. 9, 2007. These applications are incorporated herein by reference in their entirety for all purposes.

GOVERNMENT RIGHTS

This invention was made with Government support under contract number BES-0529048 awarded by the National Science Foundation. The U.S. Government has certain rights in this invention.

BACKGROUND

Trichloroethene (TCE) and tetrachloroethene (perchloroethene, PCE) are the most commonly used industrial solvents and degreasers in the world. The annual U.S. consumption of TCE was 245 million pounds in 2005, with a 4.5% per year increase since then. As a consequence of its extensive use, spillage and improper disposal have resulted, and thus TCE is one of the most commonly found chemicals in contaminated sites. About 34% of the drinking water sources and most groundwater contamination sites are estimated to contain TCE, and 75% of EPA National Priority List hazardous waste sites and Superfund sites have TCE pollution. TCE is a suspected carcinogen, as well as a known kidney and liver toxin. In addition, TCE can be transformed to vinyl chloride via microbial anaerobic dehalogenation in groundwater, increasing the concerns regarding TCE contamination in groundwater.

TCE concentration measurement using gas chromatography (GC) is the most popular TCE detection method with good selectivity and low limits of detection (LOD), as low as 0.02 μg/L using EPA method 8260b for volatile organic compounds, while absorption spectroscopy based techniques (e.g., Fourier transform infrared spectroscopy) can also detect trace amounts of TCE with short acquisition times and high signal-to-noise ratios. However, these methods are time-consuming and expensive, and additional pre-treatment steps are often required prior to sample analysis.

Biosensors have the potential to be excellent alternatives or complements to traditional analytical chemical methods for environmental monitoring. By integrating a biological process and transduction, a biosensor is capable of real-time analysis with simplicity of operation. In a biosensor system, enzymes have benefits as the biocomponents due to their high sensitivity and good specificity, while optical transduction has potential advantages over electrical transduction in environmental monitoring because of low signal losses over long distance as well as not requiring a reference signal. Biosensors are often reagentless, and can thus provide continuous, in-situ measurements as a cost-effective alternative compared with traditional analytical methods.

SUMMARY

In one aspect, a biosensing system is disclosed that measures the concentration of a halogenated alkene in a solution and comprises a first biocomponent that catalyzes the reaction of a halogenated alkene, and a second biocomponent that catalyzes the reaction of a halogenated alkene epoxide. The biosensing system also includes a transducer layer that luminesces and produces photons and is part of an optode.

In another aspect, a method for measuring the concentration of a halogenated alkene in a solution is disclosed whereby a first biocomponent catalyzes the reaction of a halogenated alkene and oxygen, and a second biocomponent catalyzes the reaction of a halogenated alkene epoxide produced by the first biocomponent; and whereby a transducer layer luminesces and the luminescence of the transducer layer is altered by oxygen in the solution; and whereby the photons produced by the luminescence of the transducer layer enter into a fiber optic cable and are transmitted to a photomultiplier, whereby the photomultiplier produces an output signal that is coupled to an algorithm that transforms the signal generated by the photomultiplier into an output correlated to the concentration of the halogenated alkene in the solution. In one embodiment, the first biocomponent is selected from the group consisting of toluene ortho-monoxygenase (EC 1.13.12), a toluene ortho-monoxygenase variant, a toluene dioxygenase (EC 1.14.12.11), and toluene ortho-monoxygenase-Green. In one embodiment, the second biocomponent is selected from the group consisting of epoxide hydrolase (EC 3.3.2.10), glutathione synthetase (EC 6.3.2.3), glutathione S-transferase (EC 2.5.1.18) and gamma-glutamylcysteine synthetase (EC 6.3.2.2). In one embodiment, the transducer layer is RuDPP and/or fluorescein.

In an aspect of the disclosure, a biosensing system that measures the concentration of halogenated alkenes in a solution comprises a first biocomponent that catalyzes the reaction of a halogenated alkene and oxygen and a second biocomponent that catalyzes the reaction of a halogenated alkene epoxide created by the reaction of the first biocomponent with the halogenated alkene. The biosensing system also comprises a transducer layer that luminesces and the luminescence of the transducer layer is altered by oxygen in the solution; and the photons produced by the luminescence of the transducer layer enter into a fiber optic cable and are transmitted to a photomultiplier where the photomultiplier produces an output signal that is coupled to an algorithm that transforms the signal generated by the photomultiplier into an output correlated to the concentration of the halogenated alkene in the solution. In an embodiment, the halogenated alkene is selected from the group consisting of tetrachloroethene, trichloroethene, dichloroethene isomers, and monochloroethene. In one embodiment, the first biocomponent is selected from the group consisting of toluene ortho-monoxygenase, and toluene ortho-monoxygenase-Green, and toluene dioxygenase. In one embodiment, the second biocomponent is selected from the group consisting of epoxide hydrolase, glutathione synthetase, glutathione S-transferase and gamma-glutamylcysteine synthetase. In an embodiment, the transducer layer is RuDPP and/or fluorescein.

In an aspect of the present disclosure, a biosensing element is disclosed that measures the concentration of a halogenated alkene in a solution. The tip comprises a first biocomponent that catalyzes the reaction of the halogenated alkene and a second biocomponent that catalyzes the reaction of a halogenated alkene epoxide. The first biocomponent and said second biocomponent comprise cells that contain enzymes selected from the group consisting of oxygenases, monooxygenases, dioxygenases, toluene ortho-monoxygenase-Green, toluene dioxygenase, epoxide hydrolase, glutathione synthetase, glutathione S-transferase and gamma-glutamylcysteine synthetase. The cells are immobilized within a matrix that is in contact with a transducer layer. The transducer layer is part of an optode. In one embodiment, cells are alive. In an embodiment, cells are dead. In an embodiment, the transducer layer is an optical transducer that interacts with oxygen. In another embodiment, the transducer layer comprises RuDPP and/or fluorescein.

In one aspect, a biosensing element that measures the concentration of trichloroethene in a solution is disclosed. The biosensing element comprises a first biocomponent that catalyzes the reaction of trichloroethene and oxygen and a second biocomponent that catalyzes the reaction of trichloroethene epoxide. The biosensing element also comprises a transducer layer that luminesces and the luminescence of the transducer layer is altered by oxygen in the solution; and the photons produced by the luminescence of the transducer layer enter into a fiber optic cable and are transmitted to a photomultiplier wherein the photomultiplier produces an output signal that is coupled to an algorithm that transforms the signal generated by the photomultiplier into an output correlated to the concentration of trichloroethene in the solution. In one embodiment, the first biocomponent is selected from the group consisting of toluene ortho-monoxygenase, toluene ortho-monoxygenase-Green and toluene dioxygenase. In another embodiment, the second biocomponent is selected from the group consisting of epoxide hydrolase, glutathione synthetase, glutathione S-transferase and gamma-glutamylcysteine synthetase. In one embodiment, the transducer layer is RuDPP.

In one aspect, a method is disclosed for measuring the concentration of trichloroethene in a solution wherein a first biocomponent selected from the group consisting of toluene ortho-monoxygenase and toluene ortho-monoxygenase-Green catalyzes the reaction of trichloroethene and produces trichloroethene epoxide; and wherein a second biocomponent selected from the group consisting of epoxide hydrolase, glutathione synthetase, glutathione S-transferase and gamma-glutamylcysteine synthetase catalyzes the reaction of trichloroethene epoxide; and wherein a transducer layer luminesces and the luminescence of the transducer layer is altered by oxygen in the solution; and the photons produced by the luminescence of the transducer layer enter into a fiber optic cable and are transmitted to a photomultiplier that produces an output signal that is coupled to an algorithm that transforms the signal generated by the photomultiplier into an output correlated to the concentration of trichloroethene or other halogenated hydrocarbons in the solution.

In one aspect, a biosensing element is disclosed that measures the concentration of trichloroethene in a solution. The biosensing element comprises a first biocomponent that catalyzes the reaction of trichloroethene and a second biocomponent that catalyzes the reaction of trichloroethene epoxide. The first biocomponent and the second biocomponent comprise cells that contain enzymes from the group consisting of toluene ortho-monoxygenase, toluene ortho-monoxygenase-Green, epoxide hydrolase, glutathione synthetase, glutathione S-transferase and gamma-glutamylcysteine synthetase. The cells are immobilized within a matrix that is in contact with a transducer layer. The transducer layer is part of an optode. In an embodiment, the cells are alive. In another embodiment, the cells are dead. In an embodiment, the transducer layer is a chemical transducer that interacts with oxygen. In an embodiment, the transducer layer is an optical transducer that interacts with oxygen.

In one aspect, a method for constructing biosensing systems having a linear response to the concentration of an analyte in a solution is disclosed wherein the biosensing system has an optode, and the optode has a fiber optical cable having a first tip and a second tip, and the first tip is covered by a transducer layer, and the transducer layer is covered by a biocomponent layer, and the biocomponent layer is covered by a porous layer, and the second tip is coupled to a photon-detection device, and the photon-detection device is coupled to a signal processing system, and the analyte concentration in the solution, the depth of the biocomponent layer, the depth of the porous layer, the diffusion coefficient of the porous layer, the $K_m$ and $V_{max}$ of the reaction of the analyte that is catalyzed by the biocomponent and the analyte are selected such that the quotient between $Da^2$ and $4\beta$ is from about 10 to about 1000. In one embodiment, the biocomponent is toluene ortho-monooxygenase. In one embodiment, the biocomponent is a toluene ortho-monooxygenase variant. In one embodiment, the analyte is trichloroethene. In another embodiment, the biocomponent has both a toluene ortho-monooxygenase variant and formate dehydrogenase, and also has at least one enzyme selected from an epoxide hydrolase, a glutathione synthetase, a glutathione S-transferase and a gamma-glutamylcysteine synthetase. In one embodiment, the transducer layer is RuDPP. In one embodiment, the porous layer is track-etched polycarbonate.

In one aspect, a biosensing system for measuring the concentration of an analyte in a solution is disclosed wherein the biosensing system has an optode, and the optode has a fiber optical cable having a first tip and a second tip, and the first tip is covered by a transducer layer, and the transducer layer is covered by a biocomponent layer, and the biocomponent layer is covered by a porous layer, and the second tip is coupled to a photon-detection device, and the photon-detection device is coupled to a signal processing system, and the analyte concentration in the solution, the depth of the biocomponent layer, the depth of the porous layer, the diffusion coefficient of the porous layer, the $K_m$ and $V_{max}$ of the reaction between the biocomponent and the analyte are selected such that the quotient between $Da^2$ and $4\beta$ is from about 10 to about 1000. In one embodiment, the biocomponent is toluene ortho-monooxygenase. In one embodiment, the biocomponent is a toluene ortho-monooxygenase variant. In one embodiment, the analyte is trichloroethene. In another embodiment, the biocomponent has both a toluene ortho-monooxygenase variant and formate dehydrogenase, and also has at least one enzyme selected from an epoxide hydrolase, a glutathione synthetase, a glutathione S-transferase and a gamma-glutamylcysteine synthetase. In one embodiment, the transducer layer is RuDPP. In one embodiment, the porous layer is track-etched polycarbonate.

In an aspect, a biosensing system is disclosed that measures the concentration of a halogenated alkene in a solution and contains a biocomponent that catalyzes the reaction of the halogenated alkene, and a transducer layer that luminesces and is part of an optode.

In another aspect, a method for measuring the concentration of a halogenated alkene in a solution is disclosed wherein a biocomponent catalyzes the reaction of the halogenated alkene and oxygen, and where a transducer layer luminesces, and the transducer layer luminescence is altered by oxygen and/or hydrogen ions in the solution, and the photons from the luminescence of the transducer layer enter into a fiber optic cable and are transmitted to a photomultiplier, and the photomultiplier produces an output signal that is coupled to an algorithm that transforms the signal generated by the photomultiplier into an output correlated to the concentration of the halogenated alkene in the solution. In an embodiment, the biocomponent is selected from the group consisting of toluene ortho-monoxygenase, toluene ortho-monoxygenase-Green, toluene ortho-monoxygenase variant, and toluene dioxygenase. In another embodiment, the transducer layer is selected from the group consisting of RuDPP and fluorescein.

In an aspect, a biosensing system is disclosed that measures the concentration of halogenated alkenes in a solution and has a biocomponent that catalyzes the reaction of a halogenated alkene and oxygen, and a transducer layer that luminesces, and the transducer layer luminescence is altered by oxygen and/or hydrogen ions in said solution, and the photons from the luminescence of said transducer layer enter into a fiber optic cable and are transmitted to a photomultiplier, and the photomultiplier produces an output signal that is coupled to an algorithm that transforms the signal generated by said photomultiplier into an output correlated to the concentration of said halogenated alkene in the solution. In one embodiment, the biosensing system for halogenated alkenes is selected from the group consisting of tetrachloroethene, trichloroethene, dichloroethene, and monochloroethene. In another embodiment, the biosensing system has a biocomponent that is selected from the group consisting of toluene ortho-monoxygenase, toluene ortho-monoxygenase-Green, toluene ortho-monoxygenase variant, and toluene dioxygenase. In yet another embodiment, the biosensing system has a transducer layer that is selected from the group consisting of RuDPP and fluorescein.

DETAILED DESCRIPTION

Figure 1:
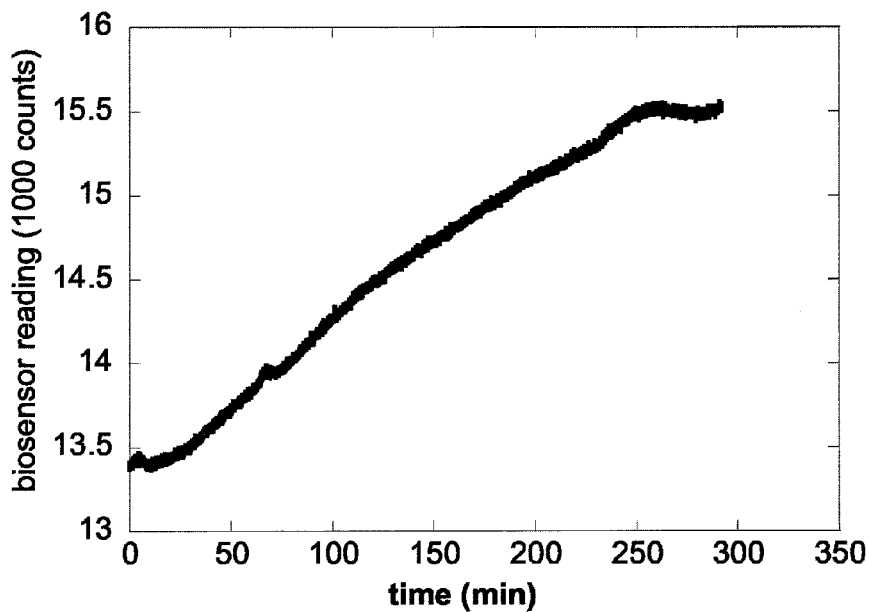
FIG. 1. Time course of a TOM-Green biosensing system response to the addition of 0.61 mg/L TCE.

Biosensing systems offer the potential of measurements that are specific, continuous, rapid, and reagentless. Biosensing elements of biosensing systems combine a biocomponent which is coupled to a transducer to yield a device capable of measuring chemical concentrations. A biocomponent may be any biological detection agent. Examples of biocomponents include enzymes, whole cells, microorganisms, RNA, DNA, aptamers and antibodies. The biocomponent interacts with an analyte via a binding event and/or reaction. The role of the transducer is to convert the biocomponent detection event into a signal, usually optical or electrical. A transducer is typically a physical sensor such as an electrode, or a chemical sensor. The analyte normally interacts with the biocomponent through a chemical reaction or physical binding. For example, in the case of a biosensing system that uses an enzyme biocomponent, the enzyme biocomponent would react with the analyte of interest and a product or reactant of the enzyme catalyzed reaction such as oxygen, ammonia, hydrochloric acid or carbon dioxide, may be detected by an optical, electrochemical or other type of transducer.

In one embodiment of the present disclosure, biosensing systems contain a second biocomponent enzyme that catalyzes the reaction of reactive products created by the reaction of a first biocomponent enzyme with an analyte of interest. The second biocomponent enzyme catalyzes the reaction of the reactive product and prevents a decrease in activity of the first biocomponent caused by the reactive product reacting with active site residues or other residues that render the first biocomponent less active or inactive.

In one embodiment, biocomponents of the biosensing system are monooxygenases Enzyme Commission number (EC) 1.13 and/or dioxygenases EC 1.14. In one embodiment, toluene ortho-monooxygenase (TOM) and/or toluene ortho-monooxygenase-Green (TOM-Green, a toluene ortho-monooxygenase variant) are used as a biocomponent. In one embodiment, toluene diooxygenase (TDO) is used as a biocomponent. Genes for the enzymes TOM and/or TOM-Green and/or TDO may be cloned into plasmids and then introduced into *Escherichia coli* (*E. coli*) or may also be cloned directly into the chromosomal DNA of *E. coli*. The *E. coli* containing plasmids with genes encoding TOM and/or TOM-Green and/or TDO may be used as biocomponents. These genes may also be encoded naturally on plasmid or chromosomal DNA in certain microorganisms that are useful as biocomponents. In one embodiment, these genes may be introduced to other suitable organisms such as other bacteria, archaea or eukaryotes.

In one embodiment, biocomponents of the biosensing system are monooxygenases Enzyme Commission number (EC) 1.13 and/or dioxygenases EC 1.14. In one embodiment, toluene ortho-monooxygenase (TOM) and/or toluene ortho-monooxygenase-Green (TOM-Green, a toluene ortho-monooxygenase variant) are used as a biocomponent. Genes for the enzymes TOM and/or TOM-Green may be cloned into plasmids and then introduced into their native host, such as *Burkholderia cepacia* G4, for example, or may also be cloned directly into the chromosomal DNA of their native host. The native hosts containing these plasmids with genes encoding TOM and/or TOM-Green may be used as biocomponents. These genes may also be encoded naturally on plasmid or chromosomal DNA in the native host microorganisms that are useful as biocomponents.

Advantages in using biosensing systems for measuring analytes include fast measurement, generally on the order of minutes. This is a big advantage over traditional methods like GC or HPLC in which a lot of time is spent in collection of the sample and extraction of analytes from the sample.

Small size is another advantage of using biosensing systems. Biosensing systems of the present disclosure have a compact design and are therefore capable of measurements in confined places such as needles and catheters in vivo and in conditions where weight is critical like spacecraft or airplanes.

An advantage of using biosensing systems is that they can be used to measure multiple analytes. Yet another advantage of using biosensing systems is that they can be used in a continuous real-time measurement. Biosensing systems disclosed herein may be used in a reversible manner with extremely low signal loss. Furthermore, biosensing systems are capable of measuring at depths for applications such as groundwater monitoring. Biosensing systems disclosed herein can make measurements in situ.

An important advantage is the ability of biosensing systems to measure complex samples with no prior preparation of samples. Biosensing systems can provide direct measurements in blood, food, and waste water, for example. This is important as removal of the sample from its environment (as in case of analyses by GC or HPLC) can change its chemistry and can thereby lead to inaccurate results. Also, this eliminates and simplifies sample separation steps and reduces the cost of the process. Measurements using biosensing systems can be made with minimum perturbations of the sample.

Biosensing systems have high specificity and sensitivity for measuring analytes of interest. Although most of the traditional methods (GC or HPLC) are very sensitive, they require expensive, laboratory-based hardware and trained operators. Other methods such as solid-phase enzyme-linked immunoassay (ELISA) may have good sensitivity but are generally not highly specific.

Another advantage for using biosensing systems of the present disclosure is the low cost of mass production compared to most of the traditional methods like GC or HPLC. Biosensing systems of the present disclosure are easy to use compared to traditional monitoring techniques such as gas chromatography, ion chromatography and high-pressure liquid chromatography. Biosensing systems using the proper biocomponents can also measure the toxicity of chemicals whereas analytical methods such as GC and HPLC can only measure concentration.

DEFINITIONS

Amperometric: Amperometric pertains to measurement of an electrical current.

Halogenated alkene: A halogenated alkene is a hydrocarbon chemical with at least one double bond and in which one or more halogen atoms are substituted for hydrogen atoms. The halogen atoms may be fluorine, chlorine, bromine, and/or iodine. Non-limiting examples of halogenated alkenes include tetrachloroethene, trichloroethene, dichloroethene and monochloroethene and isomers thereof. Trichloroethene may also be referred to as trichloroethylene. In general, a halogenated ethene compound may also be referred to as a halogenated ethylene compound.

Dichloroethene: As used herein, "dichloroethene" includes the isomers 1,1-dichloroethene, cis-1,2-dichloroethene, and trans-1,2-dichloroethene. As used herein, the term "dichloroethene" is synonymous with dichloroethenes. The term "dichloroethenes" includes 1,1-dichloroethene, cis-1,2-dichloroethene, trans-1,2-dichloroethene, and dichloroethene.

Halogenated hydrocarbon: A halogenated hydrocarbon is a hydrocarbon chemical in which one or more halogen atoms are substituted for hydrogen atoms. The halogen atoms may be fluorine, chlorine, bromine, and/or iodine.

Oxygenases: An oxygenase is any enzyme that oxidizes a substrate by transferring the oxygen from molecular oxygen ($O_2$) to it. The oxygenases form a class of oxidoreductases (EC 1); their EC number is EC 1.13 or EC 1.14. There are two types of oxygenases, monooxygenases and dioxygenases.

Monooxygenase: Monooxygenases are enzymes that incorporate one hydroxyl group into substrates in many metabolic pathways. The oxygen atom in the hydroxyl originates from molecular oxygen ($O_2$). Generally, in the reaction catalyzed by monooxygenases, two atoms of dioxygen are reduced to one hydroxyl group and one $H_2O$ molecule by the concomitant oxidation of NAD(P)H. Monooxygenases are a type of oxygenases.

Dioxygenase: Dioxygenases, or oxygen transferases, are enzymes that incorporate both oxygen atoms from molecular oxygen ($O_2$) into the substrate of the reaction. Dioxygenases are a type of oxygenases.

Toluene dioxygenase: Toluene dioxygenase is a class of enzymes that belong to the family of oxidoreductases EC 1, specifically to EC 1.14 and more specifically to EC 1.14.12.11. Toluene dioxygenases, for example, catalyze the chemical reaction of substrates toluene and NADH and $H^+$ and $O_2$ to the products (1S,2R)-3-methylcyclohexa-3,5-diene-1,2-diol and $NAD^+$. Toluene dioxygenase is an oxidoreductase that acts on paired electron donors with $O_2$ as an oxidant and the incorporation or reduction of oxygen. Toluene dioxygenase is synonymous with toluene 2,3-dioxygenase.

Toluene ortho-monooxygenase: Toluene ortho-monooxygenase (TOM) is an enzyme that belongs to the family of oxidoreductases EC 1, specifically to EC 1.13 and more specifically to EC 1.13.12. TOM oxidizes many substrates, including o-xylene, m-xylene, p-xylene, toluene, benzene, ethyl benzene, styrene, naphthalene, trichloroethene as well as tetrachloroethene. TOM uses oxygen and NADH as a cofactor to oxidize its substrate.

Toluene ortho-monooxygenase variant: Toluene ortho-monooxygenase (TOM) variants refer generally to any variant of TOM that has altered substrate binding kinetics, a faster turnover rate or other improved enzymological parameters over native TOM. One example of a TOM variant is TOM-Green, which has a valine to alanine substitution (V106A) in the hydroxylase alpha-subunit of TOM from *Burkholderia cepacia* G4.

NAD: NAD (nicotinamide adenine dinucleotide) used herein includes the oxidized form $NAD^+$ and the reduced form NADH. NAD is a cofactor.

NADP: NADP (nicotinamide adenine dinucleotide phosphate) used herein includes the oxidized form $NADP^+$ and the reduced form NADPH. NADP is a cofactor.

NAD(P)H: NAD(P)H is an inclusive term that embodies both the reduced form of nicotine adenine dinucleotide, NADH, and the reduced form of phosphorylated NADH, NADPH. NAD(P)H is a cofactor.

FAD: FAD (Flavin Adenine Dinucleotide) used herein includes FAD (fully oxidized form, or quinone form) that accepts two electrons and two protons to become $FADH_2$ (hydroquinone form). $FADH_2$ can then be oxidized to the semireduced form (semiquinone) FADH by donating one electron and one proton. The semiquinone is then oxidized once more by losing an electron and a proton and is returned to the initial quinone form, FAD. FAD is a cofactor.

FMN: FMN (Flavin Mononucleotide) used herein includes FMN (fully oxidized form), or FMNH (semiquinone form), and $FMNH_2$ (fully reduced form). FMN is a cofactor. In one embodiment, FMN is a prosthetic group for oxidoreductases.

Cofactor: A cofactor used herein is a non-protein chemical compound that is bound to a protein and is required for the protein's biological activity. Non-limiting examples of cofactors include: thiamine pyrophosphate, reduced and oxidized forms of flavin adenine mononucleotide (FAD), reduced and oxidized forms of flavin adenine mononucleotide (FMN), reduced and oxidized forms of nicotinamide adenine dinucleotide (NAD), reduced and oxidized forms of nicotinamide adenine dinucleotide phosphate (NADP), pyridoxal phosphate, lipoamide, methylcobalamin, cobalamine, biotin, coenzyme A, tetrahydrofolic acid, menaquinone, ascorbic acid, flavin adenine dinucleotide, coenzyme F420, adenosine triphosphate, S-adenosyl methionine, coenzyme B, coenzyme M, coenzyme Q, cytidine triphosphate, glutathione, heme, methanofuran, molybdopterin, nucleotide sugars, 3'-phosphoadenosine-5'-phosphosulfate, pyrroloquinoline, quinine, tetrahydrobiopterin, and tetrahydromethanopterin. Cofactors may also include metal ions such as $Ca^{2+}$, $Zn^{2+}$, $Fe^{2+}$, $Fe^{3+}$, $Mg^{2+}$, $Ni^{2+}$, $Cu^+$, $Cu^{2+}$, $Mn^{2+}$, and iron-sulfur clusters, for example.

Dehydrogenase: A dehydrogenase is an enzyme that oxidizes a substrate by transferring one or more hydrides ($H^-$) to an acceptor, usually $NAD^+/NADP^+$ or a flavin coenzyme such as FAD or FMN.

Measurement solution: A measurement solution is a solution in which an analyte may be dissolved to make a biosensor measurement. A non-limiting example of a measurement solution is 0.15 M NaCl and 0.025 M $CaCl_2$ at pH 7.0.

Biocomponent: A biocomponent binds, catalyzes the reaction of or otherwise interacts with analytes, compounds, atoms or molecules thereby generating an atom, molecule or compound. Non-limiting examples of biocomponents include aptamers, DNA, RNA, proteins, enzymes, antibodies, cells, whole cells, tissues, single-celled microorganisms, and multicellular microorganisms. A biocomponent may be a cell, microorganism, cell organelle or any other membrane bound container that contains biocomponent enzymes within. A biocomponent may be purified or otherwise substantially isolated biocomponent enzymes. A biocomponent may be an unpurified extract of cells containing biocomponent enzymes.

Analyte: An analyte is the substance or chemical constituent that is desired to be detected or measured, such as the analyte concentration. With enzymatic biosensors, the analyte itself is not measured. Rather, a reaction of the analyte that is catalyzed by an enzymatic biocomponent causes a change in the concentration of a reactant or product that is measureable by the biosensing system. An analyte may also be a substrate of an enzyme.

Transducer: A transducer is a substance that interacts with the atoms, compounds, or molecules produced or used by the biocomponent. The interaction of the transducer with the atoms, compounds, or molecules produced or used by the biocomponent causes a signal to be generated by the transducer layer. The transducer layer may also generate a signal as an inherent property of the transducer. The signal may be an electrical current, a photon, a luminescence, or a switch in a physical configuration. In one embodiment, the signal produced by the transducer is altered by a reactant or product of the biocomponent or may also be altered by a molecule such as oxygen.

Chemical transducer: A chemical transducer is a chemical that interacts with an atom, molecule or compound and that interaction causes the production of a proton, oxygen molecule, luminescent event, photon or other atoms and molecules.

Optical transducer: An optical transducer is a material that luminesces. An optical transducer interacts with an atom, molecule, photon or compound and that interaction causes a change in the intensity and/or lifetime of the fluorescence of the optical transducer.

Physical transducer: A physical transducer is a material that interacts with an atom, molecule, photon or compound and that interaction causes a shift in its physical properties.

Biosensor: A biosensor measures the concentration of compounds, atoms or molecules using a biocomponent. A biosensor may also detect compounds, atoms or molecules using a biocomponent. A biosensor may also measure the toxicity of compounds, atoms or molecules using a biocomponent. A biosensor may alternatively be referred to as a biosensing system and/or a biosensing element.

Biosensing system: A biosensing system contains a biosensing element, a transducer, and a signal processing system. A biosensing system may alternatively be referred to as a biosensor system. Biosensing system may alternatively refer to various parts of the biosensing system such as the biosensing element, for example. A biosensing system may also contain a biosensing element, an optode, and a signal processing system.

Biosensing element: A biosensing element detects analytes. A biosensing element comprises one or more biocomponents and a transducer. In certain embodiments, a biosensing element comprises one or more biocomponents, a transducer and/or an optode.

Crosslinking: Crosslinking is the process of linking a biocomponent to a matrix. Crosslinking may be through chemical bonds, ionic interactions, physical entrapment or other modes and methods of linking a biocomponent to a matrix.

Matrix: A matrix is an interlacing, repeating cell, net-like or other structure that embodies the biocomponents. The immobilization material is an example of a matrix. A matrix may be a polymer.

Immobilization material: Immobilization material is the substance, compound or other material used to immobilize the biocomponent onto the biosensing element transducer layer. The immobilization material may be a matrix or may be less ordered than a matrix. The immobilization material may be a polymer such as cellulose acetate, polycarbonate, collage, acrylate copolymers, poly(ethylene glycol), polytetrafluoroethylene (PTFE), agarose, alginate, polylysine, alginate-polylysine-alginate microcapsule, algal polysaccharides, agar, agarose, alginate, and carrageenan, polyacrylamide, polystyrene, polyurethane and other naturally occurring and synthetic polymers.

Polymer: Polymers as used herein include any natural or synthetic polymer including cellulose acetate, polycarbonate, collage, acrylate copolymers, poly(ethylene glycol), polytetrafluoroethylene (PTFE), agarose, alginate, polylysine, alginate-polylysine-alginate microcapsule, algal polysaccharides, agar, agarose, alginate, and carrageenan, polyacrylamide, polystyrene, polyurethane and other naturally occurring and synthetic polymers. Polymers may be used to create a diffusivity barrier between the bulk solution and a biocomponent of a biosensing system. A polymer may be a porous layer.

Optode: An optode is a sensor device that measures the concentration of a specific substance usually with the aid of a transducer. An optode can be an optical sensor device that optically measures the concentration of a specific substance usually with the aid of a transducer. In one embodiment, for example, an optode requires a transducer, a polymer to immobilize the transducer and instrumentation such as optical fiber, a light source, detectors and other electronics. Optodes can apply various optical measurement schemes such as reflection, absorption, an evanescent wave, luminescence (for example fluorescence and phosphorescence), chemiluminescence, and surface plasmon resonance. Optodes may be fiber optical cable, planar wave guides or other surfaces conducive to the propagation of total internally reflecting light waves. An optode may be an optical transducer such as a photon detector.

pH sensor: A pH sensor measures the concentration of hydrogen ions in a solution.

pH optode: A pH optode is an optode that has a detection element that interacts with hydrogen ions. Examples of detection elements that interact with hydrogen ions are fluorescein, fluoresceinamine and other fluorescein-containing compounds. In an embodiment, for example, a pH optode based on luminescence has a luminescent reagent that is pH responsive.

Luminescence: Luminescence is a general term which describes any process in which energy is emitted from a material at a different wavelength from that at which it is absorbed. Luminescence may be measured by intensity and/or by lifetime decay. Luminescence is an umbrella term covering fluorescence, phosphorescence, bioluminescence, chemiluminescence, electrochemiluminescence, crystalloluminescence, electroluminescence, cathodoluminescence, mechanoluminescence, triboluminescence, fractoluminescence, piezoluminescence, photoluminescence, radioluminescence, sonoluminescence, and thermoluminescence.

Fluorescence: Fluorescence is a luminescence phenomenon in which electron de-excitation occurs almost spontaneously, and in which emission from a luminescent substance ceases when the exciting source is removed. Fluorescence may be measured by intensity and/or by lifetime of the decay.

Fluorescein: Fluorescein is a fluorophore. In water, fluorescein has an absorption maximum at 494 nm and emission maximum of 521 nm. As used herein, the term "fluorescein" includes isomers, analogs and salts of fluorescein including, but not limited to, fluoresceinamine, resorcinolphthalein, C.I. 45350, solvent yellow 94, D & C yellow no. 7, angiofluor, Japan yellow 201, soap yellow, uranine, D&C Yellow no. 8 and fluorescein isothiocyanate.

Phosphorescence: Phosphorescence is a luminescence phenomenon in which light is emitted by an atom or molecule that persists after the exciting source is removed. It is similar to fluorescence, but the species is excited to a metastable from which a transition to the initial is forbidden. Emission occurs when thermal energy raises the electron to a from which it can de-excite. Phosphorescence may be measured by intensity and/or by lifetime of the decay.

Oxygen sensor: An oxygen sensor measures, or is responsive to, the concentration of oxygen in a solution.

Oxygen optode: An oxygen optode is an optode that has a transducer layer that interacts with oxygen. An example of a transducer layer that interacts with oxygen is tris(4,7-diphenyl-1,10-phenanthroline)Ru(II) chloride, also known as RuDPP.

Photon-detection device: A photon-detection device is a class of detectors that multiply the current produced by incident light by as much as 100 million times in multiple dynode stages, enabling, for example, individual photons to be detected when the incident flux of light is very low. Photon-detection devices may be vacuum tubes, solid photomultipliers or other devices that interact with incident light, and amplify or otherwise process the signal and/or photons produced by that interaction. Alternative embodiments of a photon-detection device include an image sensor, CCD sensors, CMOS sensors, photomultiplier tubes, charge coupled devices, photodiodes and avalanche photodiodes.

Signal processing system: A signal processing system processes the signal from a biosensing system into information that can be displayed to an end user. An example of a signal processing system is a photon-detection device that detects the photons from the output of a photo optical cable of the optode of the biosensing system. The output of the photon-detection device is coupled to the input of a converter or sampler device such as a signal processor or a transimpedance amplifier. The output of the converter or sampler device is coupled to the input of a microprocessor that processes the output of the converter or sampler device into an output corresponding to the concentration of an analyte within the solution that was measured by the biosensing system. The output of the microprocessor is then communicated to an end user, for example by displaying the concentration on a screen.

Image sensor: An image sensor is a device that converts an optical image to an electric signal. Examples of image sensors include charge-coupled devices (CCD) or complementary metal-oxide-semiconductor (CMOS) active pixel sensors.

Sampler device: A sampler device reduces a continuous signal to a discrete signal. A common example is the conversion of a sound wave or light wave (a continuous signal) to a sequence of samples (a discrete-time signal).

Avalanche photodiode: An avalanche photodiode (APD) is a highly sensitive semiconductor electronic device that exploits the photoelectric effect to convert light to electricity. APDs can be thought of as photodetectors that provide a built-in first stage of gain through avalanche multiplication.

Converter: A converter is a current-to-voltage converter, and is alternatively referred to as a transimpedance amplifier. A converter is an electrical device that takes an electric current as an input signal and produces a corresponding voltage as an output signal. In another embodiment a converter may be a voltage-to-current converter.

Biocomponents

Biocomponents react with, bind to or otherwise interact with an analyte. Reactive biocomponents produce or react with atoms, molecules or compounds that interact with the transducer.

Enzymes are proteins that can serve as biocomponents that catalyze reactions of their substrates. Substrates may be analytes. The products or reactants of the enzymatic reactions are usually measured by the biosensing system. In one embodiment, the products of the substrates that react with the analyte may themselves be acted upon and thereby produce additional products which may be measured by the biosensing system. Therefore, a biosensing system may measure primary, secondary or even higher orders of products caused by an initial reaction or binding of the analyte with the biocomponent.

Generally, enzymes for use in biosensing systems may be disposed within whole cells or extracted from cells and purified. Whole cells and microorganisms are also biocomponents and are generally less expensive than purified enzymes and may provide an environment for longer enzyme stability. The cells and organisms used as biocomponents may or may not be living (able to replicate). Whether or not the cells are living, diffusion mechanisms and membrane-bound pumps may still be active that allow for the exchange of analytes and other compounds with the environment of the cell. It is often advantageous to use dead cell or dead microorganisms or substantially purified enzymes as a biocomponent at least because the proteolytic enzymes and pathways operating in a living cell generally cease to function and the enzymes, for example, that are responsible for binding or reacting with the analytes therefore last longer than they would in a living cell. Another advantage of using dead cells or microorganisms or substantially purified enzymes is that if the biosensing system is used in-situ, such as in-line testing of milk being produced at a factory, there can be no contamination of the sample with cells or microorganisms that may infect or adulterate the sample.

Purified enzymes may be used as a biocomponent in biosensing systems. The use of cell-free enzyme preparations may reduce the impact of unwanted side reactions. Often, the extraction, isolation and purification of a particular enzyme can be expensive. Additionally, enzymes may lose their activity when separated from their intracellular environment that provides structural proteins, co-factors, consistent pH levels, buffers and other factors that contribute to the molecular integrity of the enzyme. However, some enzymes are more robust than others. For example, enzymes isolated from extremophilic organisms such as hyperthermophiles, halophiles, and acidophiles often are more resistant to being exposed to environments substantially different from those found inside of a cell or microorganism. Extracellular enzymes are also usually more robust than enzymes that are membrane bound or solely exist within the cytosol.

An enzyme's resistance to becoming inactivated due to environmental factors, or even by the nature of the reaction that they catalyze, may be increased through mutagenic techniques. Such techniques are well known in the art and include various incarnations of changing the coding nucleotide sequence for the protein through various techniques. The proteins produced by expressing the mutagenic nucleotide sequences may then be tested for resistance to environmental factors and/or increased reactivity with substrates. Such an increase in reactivity may be due to advantageous binding specificity and/or increased kinetics of the binding and/or reaction catalyzed by the enzyme.

Methods of choosing cells and microorganisms that increase the response of the biosensing system may also be used to create biosensing systems that possess increased sensitivity, have quicker response times and last longer. Such techniques include directed evolution and using microassays to determine an increase in the production amount and/or rate of production of the molecules and/or atoms that react with the transducer layer.

Transducers

A transducer is a device that produces a measurable signal, or change in signal, upon a change in its chemical or physical environment. Transducers suited for biosensing systems that use enzymes as the biocomponent are those that interact with the reactants and/or products of the biocomponent and send a signal that is processed into a measurement reading. The nature of the interaction of the biological element with the analyte has a major impact on the choice of transduction technology. The intended use of the biosensing system imposes constraints on the choice of suitable transduction technique.

Amperometric transducers work by maintaining a constant potential on the working electrode with respect to a reference electrode, and the current generated by the oxidation or reduction of an electroactive species at the surface of the working electrode is measured. This transduction method has the advantage of having a linear response with a relatively simple and flexible design. Also, the reference electrode need not be drift-free to have a stable response. Since the signal generated is highly dependent on the mass transfer of the electroactive species to the electrode surface there can be a loss in sensitivity due to fouling by species that adsorb to the electrode surface. As a result of fouling, use of amperometric transducers is restricted where continuous monitoring is required. Enzymes, particularly oxidoreductases, are well suited to amperometric transduction as their catalytic activity is concerned with electron transfer.

Electroactive species that can be monitored at the electrode surface include substrates of a biological reaction (e.g., $O_2$, NADH), final products (e.g., hydrogen peroxide for oxidase reactions, benzoquinone for phenol oxidation) and also electrochemical mediators that can directly transfer electrons from the enzyme to the working electrode surface (e.g. hexacyanoferrate, ferrocene, methylene blue).

Potentiometric transducers work by having a potential difference between an active and a reference electrode that is measured under the zero current flow condition. The three most commonly used potentiometric devices are ion-selective electrodes (ISEs), gas-sensing electrodes and field-effect transistors (FETs). All these devices obey a logarithmic relationship between the potential difference and the activity of the ion of interest. This makes the sensors have a wide dynamic range. One disadvantage of this transducer is the requirement of an extremely stable reference electrode. Ion selective electrodes are commonly used in areas such as water monitoring. FETs are commercially attractive as they can be used to make miniaturized sensors, but manufacturing cost of FETs are high. Examples of potentiometric sensors are for acetaldehyde and cephalosporins, where the sensing electrode measures pH. Other examples are sensors used to measure creatinine, glutamine and nitrate with the sensing electrode detecting $NH_3$ gas.

Conductimetric transducers are often used to measure the salinity of marine environments. Conductance is measured by the application of an alternating current between two noble metal electrodes immersed in the solution. Due to specific enzyme reactions, they convert neutral substrates into charged products, causing a change in the conductance of the medium. This method can be used to make more selective and informative sensors by using multi-frequency techniques.

Optical transducers use optical phenomena to report the interaction of the biocomponent and the analyte. The main types of photometric behavior which have been exploited are ultraviolet and visible absorption, luminescence such as fluorescence and phosphorescence emission, bioluminescence, chemiluminescence, internal reflection spectroscopy using evanescent wave technology and laser light scattering methods.

One embodiment of an optical transducer uses luminescent reagents. In optical transducers that use luminescent reagents, a luminescent substance is excited by incident light, and as a result it emits light of longer wavelength. The intensity and/or lifetime decay of emitted light changes when an atom, molecule or compound binds or otherwise interacts with the luminescent substance. The atom, molecule or compound may be a reactant or product of the biocomponent. Thus, if a reactant or product of the biocomponent catalyzes the reaction of the luminescent transducer and affects the intensity and/or lifetime decay of the light emitted by the transducer layer, the change in the measurement of the intensity and/or lifetime decay can be measured as a response to a particular analyte. There are several luminescent reagents that may be useful as optical transducers. Examples include Tris(4,7-diphenyl-1,10-phenanthroline)Ru(II) chloride, also known as RuDPP, for oxygen sensors, trisodium 8-hydroxy-1,3,6-trisulphonate fluorescein, fluoresceinamine and other compounds containing fluorescein for pH sensors, fluoro (8-anilino-1-naphthalene sulphonate) for $Na^+$ ion sensor and acridinium- and quinidinium-based reagents for halides.

Chemiluminescent and bioluminescent sensors work on principles similar to fluorescent sensors. Chemiluminescence occurs by the oxidation of certain substances, usually with oxygen or hydrogen peroxide, to produce visible light. Bioluminescence is, for example, the mechanism by which light is produced by certain enzymes, such as luciferase.

Calorimetric transducers use the heat generated from biological reactions and correlate it with the reaction conditions. In order to measure such small amounts of heat liberated during the reaction, a very sensitive device is required. In the calorimetric technique a very sensitive, electrical resistance thermometer is used to detect temperature changes down to 0.001° C. This method is advantageous, as it is independent of the chemical properties of the sample. Calorimetric transduction has been used in a wide range of areas, including clinical chemistry, determination of enzyme activity, monitoring gel filtration, chromatography, process control and fermentation.

An acoustic transducer uses materials such as piezoelectrics as a sensor transducer due to their ability to generate and transmit acoustic waves in a frequency-dependent manner. The optimal resonant frequency for acoustic-wave transmission is highly dependent on the physical dimensions and properties of the piezoelectric crystal. Any change in the mass of the material at the surface of the crystal will cause quantifiable changes in the resonant frequency of the crystal. There are two types of mass-balance acoustic transducers: bulk wave and surface acoustic wave. Acoustic transduction is a relatively cheap technique but it has the disadvantage of having low sensitivity with non-specific binding. This technique is commonly used to measure the concentration of volatile gases and vapors. A piezoelectric immunobiosensor for measuring an analyte of interest in drinking water may use a piezoelectric crystal coated with polyclonal antibodies that bind to that analyte. When the analyte molecules come into contact with the antibodies, they bond with the antibodies causing a change in the crystal mass, which in turn leads to a shift in the oscillation frequency and produces a measurable signal that can be measured and correlated to the concentration of the analyte of interest within the sample.

Optical and Signal Processing Systems

In an embodiment, biosensing systems of the present disclosure have a biocomponent, a transducer, a photon-detection device, and a signal-processing system. A signal processing system processes the signal from a photon-detection device into information that can be displayed to an end user. An example of a signal processing system is a microprocessor that accepts an input signal from a photon-detection device that is coupled to a biosensing element. The signal processing system then uses a software program that encodes an algorithm. The algorithm used by the software transforms the data provided by the input signal and provides an output signal that correlates to a numerical display of the concentration of an analyte that the biosensing system detected.

In an embodiment of the present disclosure, a biosensing system comprises biocomponent attached to a fiber optic pH optode, lens focusing system, photomultiplier (PMT), analog/digital (A/D) converter and a microprocessor. The biosensing element may be coupled to a polymethylmethacrylate (PMMA) optical fiber optic. The length of this connecting optical fiber may vary from 1 mm to well over 1 km. In an embodiment, the other end of this cable is attached to a light emitting diode (LED). In another embodiment, the other end of this cable is attached to a metal casing containing a 5 W halogen lamp or other light source and a lens focusing system. The light source should be able to operate at high temperatures, having a very short warm-up time in order to reach a constant power output. In one embodiment, light from the halogen lamp is first passed through a bandpass filter such as a 480-nm bandpass filter, for example. The light is then collected, paralleled and focused to the tip of fiber optic cable using a lens focusing system. An embodiment of the lens focusing system comprises spheric, aspheric, and convex lenses, and a dichroic mirror. Light from the lamp that radiates in opposite directions to the lens system may be refocused by the spheric lens and paralleled by the aspheric lens.

When light, for example light at 480 nm, is incident on a sensing tip coated with PVA/fluoresceinamine dye, fluorescence occurs. In an embodiment, this light is then passed back through a 520 nm bandpass filter or other bandpass filter having a frequency of light that is either blue or red shifted in comparison to the incident light wavelength, paralleled by focusing lens and then directed by the dichroic mirror onto the window of a single channel photo-detection device. The change in intensity and/or lifetime decay properties of the light can be measured. The photon detection device processes this light and the output potentiometric signal is sent to a computer interface using a connector block where it was converted into a digital signal by a data acquisition card. The final output is observed on a computer using software such as LabView software or other algorithmic software that interprets the signals from the sensing tip and processes them into correlating concentration measurements of the atom, compound, molecule or analyte of interest.

Immobilization of the Biocomponent

In order to construct a biosensing system, the biocomponent of the biosensing element of the biosensing system needs to be bound to or otherwise in contact with the transducer. This can be achieved by immobilizing the biocomponent on to the transducer. The viability of a biosensing system depends on the processing and type of material used for immobilizing the biocomponent. The material used for immobilizing the biocomponent may be referred to as a matrix, matrix material or as an immobilizing material.

Biocomponents may be very sensitive to the immobilizing process as well as the material that is used for immobilization. The pH, ionic strength, and any other latent chemistries of the gel matrix should be compatible with the biocomponent. The reactants and products of the reaction carried by the biocomponent should not affect the material used for immobilization. The biocomponent should be effectively immobilized and there should not be any leakage of the biocomponent from the matrix during the active lifetime of the biosensing system. The immobilization material should be non-toxic and non-polluting. The material should have proper permeability to allow sufficient diffusion of substrates, products and gases. The matrix material should allow for sufficient cell activity and cell density. The immobilization material should protect the biocomponent from biotic and abiotic environmental stresses that would lower biocomponent activity or lifetime.

Techniques of Immobilization

In one embodiment, adsorption is used to immobilize the biocomponent. Many substances adsorb enzymes, cells, microorganisms and other biocomponents on their surfaces, e.g., alumina, charcoal, clay, cellulose, kaolin, silica gel and collagen. Adsorption can be classified as physical adsorption (physisorption) and chemical adsorption (chemisorption). Physisorption is usually weak and occurs via the formation of van der Waals bonds or hydrogen bonds between the substrate and the enzyme molecules. Chemisorption is much stronger and involves the formation of covalent bonds. Adsorption of the biocomponent may be specific through the interaction of some moiety, link or other reactive component of the biocomponent or may be non-specific.

In another embodiment, microencapsulation is used to immobilize the biocomponent. In this method, a thin microporous semipermeable membrane is used to surround the biocomponent. Because of the proximity between the biocomponent and the transducer and the very small thickness of the membrane, the biosensing element response is fast and accurate, and there is always an option of bonding the biocomponent to the fiber optical portion of the biosensing system via molecules that conduct electrons, such as polypyrrole, for example. The membrane used for microencapsulation may also serve additional functions such as selective ion permeability, enhanced electrochemical conductivity, mediation of electron transfer processes, or controlling the sensitivity of the response of the biosensing system. Examples of membranes that may be used for microencapsulation immobilization of biocomponents are cellulose acetate, polycarbonate, collage, acrylate copolymers, poly(ethylene glycol) and polytetrafluoroethylene (PTFE). Additional materials that may be used are agarose, and alginate and polylysine, which together form an alginate-polylysine-alginate microcapsule.

In another embodiment, entrapment is used to immobilize the biocomponent. In this method, cells are physically constrained (entrapped) to stay inside a three-dimensional matrix. The materials used for entrapment must allow uniform cell distribution, biocompatibility and good transport of substrates, cofactors and products. Both natural and synthetic materials (like alginate, agarose and collagen) may be used for entrapment.

In another embodiment, hydrogels are used to immobilize the biocomponent. Hydrogels provide a hydrophilic environment for the biocomponent and they require only mild conditions to polymerize. Hydrogels are capable of absorbing large quantities of water which can facilitate enzymatic biocomponent reactions such as hydrolysis. Both natural and synthetic hydrogels may be used such as algal polysaccharides, agar, agarose, alginate, and carrageenan, polyacrylamide, polystyrene and polyurethane.

Alginate, a hydrogel, provides a good, biocompatible microenvironment for the biocomponent and has a gentle encapsulation process. It is a naturally occurring linear polymer composed of β-(1,4) linked D-mannuronic acid and a-(1,4)-L-guluronic acid monomers. Commercially, alginate is obtained from kelp, but bacteria such as *Azotobacter vinelandii*, several *Pseudomonas* species and various algae also produce it. When alginate is exposed to $Ca^{2+}$ ions, a cross-linking network is formed by the bonding of $Ca^{2+}$ ions and polyguluronic portions of the polymer strand by a process known as ionic gelation. The gelation process is temperature-independent. Complete gelling time without biocomponents may be from about 1 minute to greater than about 30 minutes. Gelling time usually increases with an increase in biocomponent density and decreases with an increase in $CaCl_2$ concentration.

In another embodiment, sol-gels may be used to entrap biocomponents into silicate networks. Sol-gels may require milder polymerization processes and create matrices that exhibit good mass transport and molecular access properties particularly for electrochemical and optical transduction modes.

In another embodiment, cross-linking is used to immobilize the biocomponent. Cross-linking chemically bonds the biocomponent to solid supports or to other supporting materials such as a gel. Bifunctional agents such as glutaraldehyde, hexamethylene diisocyanate and 1,5-dinitro-2,4-difluorobenzene may be used to bind the biocomponent to the solid support such as a matrix, for example. Cross-linking produces long-term stability under more strenuous experimental conditions, such as exposure to flowing samples, stirring, washing, etc.

In another embodiment, covalent bonding is used to immobilize the biocomponent. Covalent bonding uses a particular group present in the biocomponent, which is not involved in catalytic action, and attaches it to the matrix, transducer layer, membrane or fiber optical surface through a covalent bond. The radicals that take part in this reaction are generally nucleophilic in nature (e.g., —$NH_2$, —COOH, —OH, —SH and imidazole groups).

Stabilization

Biosensing systems of the present disclosure are stable and long-lived, can stand prolonged storage and can also perform consistently when used for extended periods. Biocomponents may be stabilized through various means, depending upon the type of biocomponent and transducer used.

In one embodiment, the biocomponent may be stabilized through molecular modification. Molecular modification improves the stability of enzymes, and other biocomponents, through changing certain amino acids or nucleotides in the peptide or nucleic acid sequence, respectively. Molecular modifications may increase the temperature stability of various enzymes by modifying the amino acids at the catalytically active enzyme reaction site or at structurally sensitive amino acid sequences, through site-directed mutagenesis.

Another method for improving the stability of biocomponents, such as enzymes, is through glycosylation. Since glycosylated proteins are very stable, grafting or otherwise bonding polysaccharides or short chains of sugar molecules onto protein molecules usually improves the stability of the biocomponent.

In one embodiment, the biocomponent may be stabilized through cross-linking. Cross-linking of the biocomponent may occur through covalent bonding, entrapment, encapsulation and other immobilization techniques or processes. These immobilization processes can improve enzyme stability by reducing the biocomponent's mobility and thereby reducing degradation of its three-dimensional structure. In addition, cross-linking prevents the loss of biocomponents from the matrix in which they are immobilized. Using the entrapment method discussed above, the loss of biocomponents may further be reduced by the addition of certain gel-hardening agents such as glutaraldehyde, polyethyleneimine, hexamethylenediamine and formaldehyde.

In another embodiment for stabilizing the biocomponent, freeze drying, also known as lyophilization, may be used. Freeze drying is a method for long-term preservation of microorganisms and enzymes. It involves removal of water from frozen bacterial suspensions by sublimation under reduced pressure. The lyophillization is performed in the presence of cryoprotective agents such as glycerol and DMSO, which reduce the damage caused during freezing and during thawing. Lyophillized biocomponents, for example dried cells, are stable to degradation by keeping the lyophilized biocomponents below 4° C., and away from oxygen, moisture and light. Even after prolonged periods of storage, such as about 10 years, lyophillized biocomponents may then be rehydrated and restored to an active. Two examples of lyophilizing techniques used on biocomponents include centrifugal freeze-drying and prefreezing.

In another embodiment, the biocomponents by be stabilized through heat shocking. Heat shocking involves heating vacuum-dried cells at a high temperature (about 300° C., for example) for a very short time (about 2-3 minutes, for example). With the proper combination of temperature and heating time, biocomponents such as whole cells and microorganisms can be killed but still retain an active enzyme system that may be used to detect a compound of interest. These dead cells and microorganisms can be kept for a long time away from moisture without any requirement of nutrients.

In another embodiment, the addition of carbohydrates and other polymers will stabilize the biocomponents. Carbohydrates used to stabilize biocomponents include polyalcohols and various sugars such as trehalose, maltose, lactose, sucrose, glucose and galactose, for example. This stabilization may occur due to the interaction of polyhydroxyl moieties from the polyalcohols and/or sugars with water with the biocomponents, thus increasing hydrophobic interactions and keeping the biocomponents in a stable conformation.

In an additional embodiment, stabilization of the biocomponents may occur through freezing the biocomponents. When a biocomponent is frozen, the metabolic activities may be reduced considerably. Storage of the biosensing system, and/or biosensing element at temperatures at which the biocomponents remain frozen may increase the stability and life-time of the biosensing system.

Biosensing Elements

Several biosensing system designs are disclosed herein including biosensing elements on the tip of a fiber optical cable, and biosensing elements displaced upon a surface, for example. The biosensing system may be based on an optical pH or optical oxygen sensor. Oxygenases may be used alone as the biocomponent or in conjunction with other biocomponents. The biosensing elements may be separate from one another or combined into the same tip or biosensing element.

Some biosensing systems are made using food-grade enzymes and materials. These biosensing systems are advantageously used for measuring analytes in food products.

In an embodiment, the disclosures presented herein are a set of biosensing system designs based on optical transduction. Optical enzymatic biosensing system designs using an optical signal transaction are more robust and less susceptible to chemical interference than electrochemical (e.g., amperometric) methods. In one embodiment, optical pH and optical oxygen sensors (optodes) employ fluorophores that are sensitive to either protons ($H^+$ ions) or molecular oxygen. Optical enzymatic biosensing elements are formed by combining a transducer and/or optode with a biocomponent that catalyzes a reaction with the analyte and results in altered pH or oxygen.

Biosensing System Measurement at High Analyte Concentrations

Some biosensing system applications may require the measurement of relatively high analyte concentrations. Without certain modifications, these concentrations may be high enough to saturate the response of the biocomponent, meaning that all of the binding sites of an antibody or all of the enzymatic reaction sites are occupied. Under these saturating conditions, the biosensing system response is no longer dependent upon the analyte concentration and no measurement can be made.

One embodiment of the present disclosure is for optical enzymatic biosensing systems for the measurement of analytes at high concentrations. Optical enzymatic biosensing systems for the measurement of analytes at high concentrations and the concepts disclosed herein are broadly applicable for the measurement of many different kinds of analytes in solutions such as the measurement of halogenated alkenes, for example.

Figure 8:
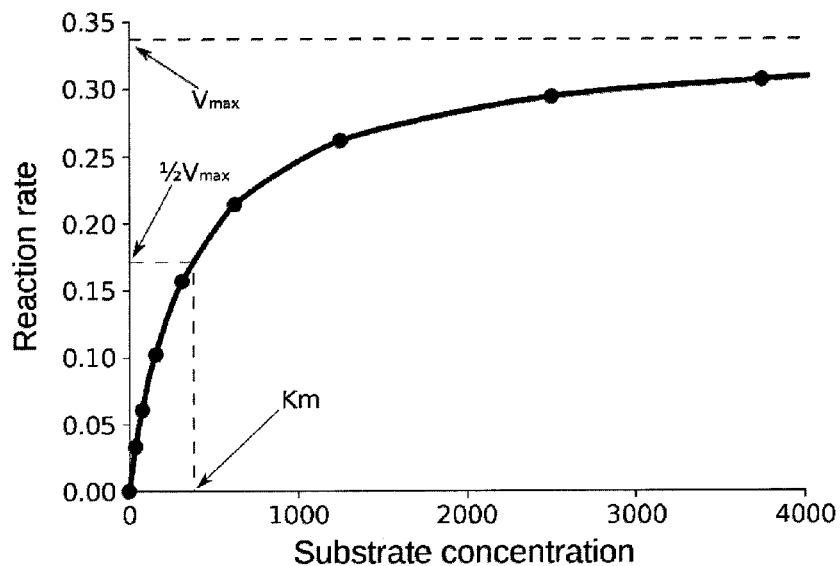
FIG. 8. Graphical representation of Michaelis-Menten equation relationships between enzyme reaction rate and substrate concentration.

Optical enzymatic biosensing systems may use biosensing elements that may be constructed as thin enzyme-containing films deposited or placed over an optical transducer layer. The response of these biosensing systems (signal as a function of analyte concentration) is governed by the rate of the enzymatic reaction and the manner in which that rate depends on the analyte concentration. For most enzymes, this relationship is the saturation type shown in FIG. 8 in which the rate depends nearly linearly on analyte concentration at low concentrations but becomes independent of concentration at high concentrations. For a biosensing system that has a biosensing element with a thin-layer biocomponent, this means that the biosensing system response becomes saturated and consequently it is not possible to distinguish one high concentration value from another.

To describe this high concentration range more accurately, it is convenient to use the Michaelis-Menten equation, which relates the enzymatic reaction rate $R_{enz}$ to the concentration of the analyte ($C_A$) as $R_{enz}=kC_E C_A/K_M+C_A$ in which k and $K_M$ are parameters of the enzymatic reaction rate (depending on the enzyme and the analyte) and $C_E$ is the concentration of enzyme. The combined term $kC_E$ is frequently presented as $V_{max}$, the maximum reaction rate ("velocity"). The Michaelis-Menten equation has been found to accurately describe many different enzyme-catalyzed reactions.

When analyte concentrations are low enough that $C_A$ is much less than $K_M$, the Michaelis-Menten equation approximately reduces to a first-order (linear) dependence of the reaction rate on the analyte concentration, $R_{enz}=(V_{max}/K_M) C_A$. This linear response is the desired operating condition for a biosensing system. However, for thin-film enzymatic biocomponent biosensing systems, this range extends only to values of $C_A$ that are small relative to $K_M$; "small" can be interpreted as 10% or less. At higher analyte concentrations, the relationship of the enzymatic reaction rate to the analyte concentration, and thus the relationship of the biosensing system response to the analyte concentration, becomes increasingly nonlinear. Once the analyte concentration becomes much larger than $K_M$ such that $C_A+K_M=C_A$, the enzymatic reaction rate and the biosensing system response become essentially independent of $C_A$. Modifying the Michaelis-Menten equation for this case of $C_A \gg K_M$ yields $R_{enz}=V_{max}$.

The analysis above is based on the assumption that the analyte concentration in the vicinity of the biocomponent enzyme molecules ("local" concentration) is the same as in the solution in which the biosensing element is placed ("bulk solution" concentration). However, this situation can be manipulated such that the local concentration is lowered such that it falls within the linear measurement range. The local concentration can be related to the bulk solution concentration by either calculating the reaction-diffusion behavior of the system or through experimental calibration procedures.

A solution to extend the linear (useful) measurement range of optical enzymatic biosensing systems beyond that available with thin-film designs is to add a mass transfer (diffusion) barrier. This diffusion barrier may take the form of a polymer coating, a membrane, or any other material through which the analyte passes more slowly than through the measurement medium. An effective diffusion barrier could also be created by increasing the thickness of the enzyme layer. Biosensing systems that have an increased thickness of the enzyme layer are generally referred to as thick-film biosensing systems. Linear measurement ranges can be extended through the use of thick-film biosensing system designs. The rates of analyte mass transfer and reaction remain coupled in thick-film biosensing system designs. Thus, at some analyte concentration, the rate of mass transfer is high enough that the analyte concentration near the enzymes exceeds the linear reaction rate range and the biosensing system no longer has a direct, linear response to the analyte concentration.

In one embodiment, biosensing systems of the present disclosure use a design scheme for the construction of optical enzymatic biosensing systems capable of measurements at high analyte concentrations. This is based on the combination of a high mass transfer resistance and a high enzyme concentration, so that the analyte concentration near the transducer/fluorophore layer always remains in the linear reaction rate (and biosensing system response) range.

Figure 9:
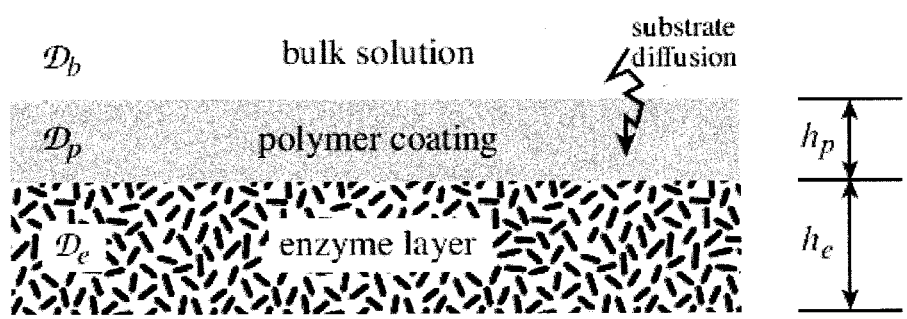
FIG. 9. Representation of optical enzymatic biosensing element portion of a biosensing system for measuring analytes in high concentrations.

For any given concentration of any particular analyte, the appropriate ranges of the mass transfer coefficient of the analyte or substrate from the bulk solution to the enzyme layer, and the reaction rate parameters of the enzyme layer can be determined according to Equation 1: $((((Da+1-\beta)^2)/4\beta) \gg 1$. Where $\beta$=the substrate concentration in the bulk solution divided by the $K_M$ of the enzyme for the substrate; and where Da is $(h_e V_{max} h_p)/(D_p K_M)$ where $h_e$ is the thickness of the enzyme layer which is embedded within a matrix; $h_p$ is the thickness of a porous polymeric or ceramic material which sits atop the enzyme layer; where $D_p$ is the diffusion coefficient of the polymer coating, see FIG. 9.

Figure 4:
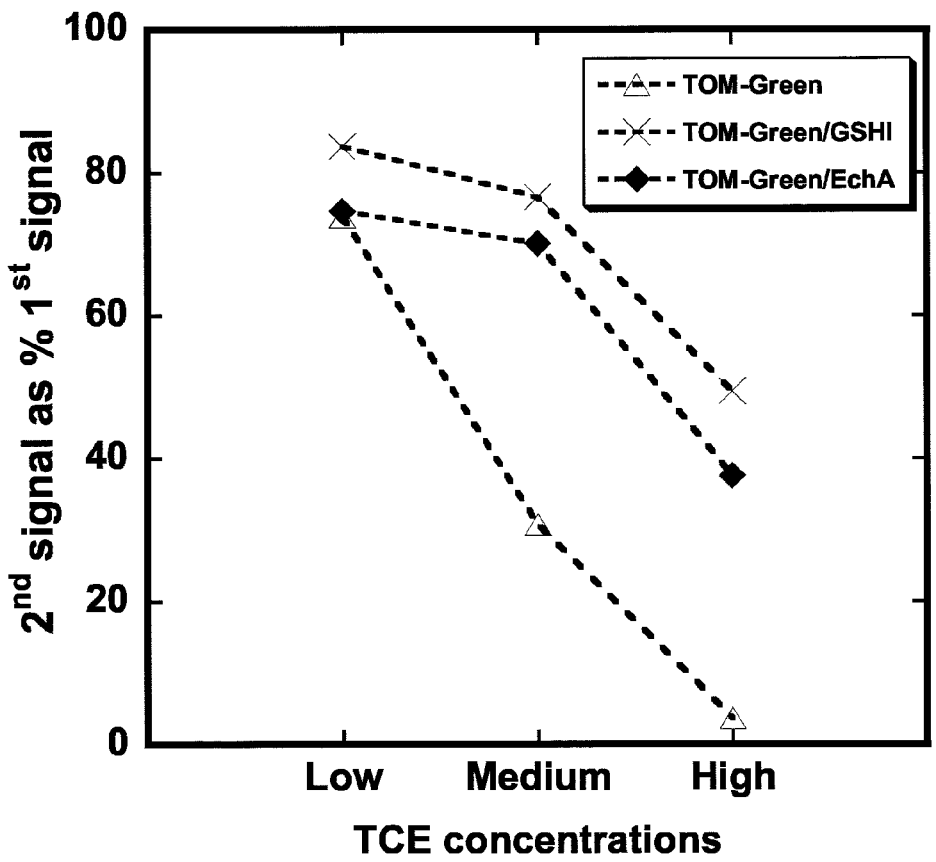
FIG. 4. Second signals as a percent of initial signals at different TCE concentrations for all three types of TOM-Green biosensing systems.

Therefore, by using Equation 1, the calculations provide specific design parameters such as the thickness of the enzymatic (detection) and mass transfer resistance layers such that a linear biosensing system response is obtained for a given concentration, see FIG. 4.

As an example of different embodiments of biosensing systems of the present disclosure, a series of biosensing systems were constructed with different membranes or no membrane covering the enzyme layer. The analyte concentration that was measured was lactose, but this series of biosensing systems is representative for any analyte or substrate, such as halogenated alkenes, for example. In one embodiment, biosensing system A, the biosensing system has only a thin film of enzyme that is immobilized on the surface of the biosensing system that is exposed to the solution. In another embodiment, biosensing system B, the biosensing system has a porous layer placed over the same thickness of enzyme layer as was used in biosensing system A. In another embodiment, biosensing system C, the same thickness of enzyme layer as biosensing systems A and B has a membrane layer placed over it that is less porous than the porous layer of biosensing system B.

Biosensing systems B and C have a membrane material consisting of track-etched polycarbonate with a pore size of 0.015 μm. Additional mass transfer resistance was provided for biosensing system C by casting a polyurethane coating on top of the porous layer material.

Figure 5:
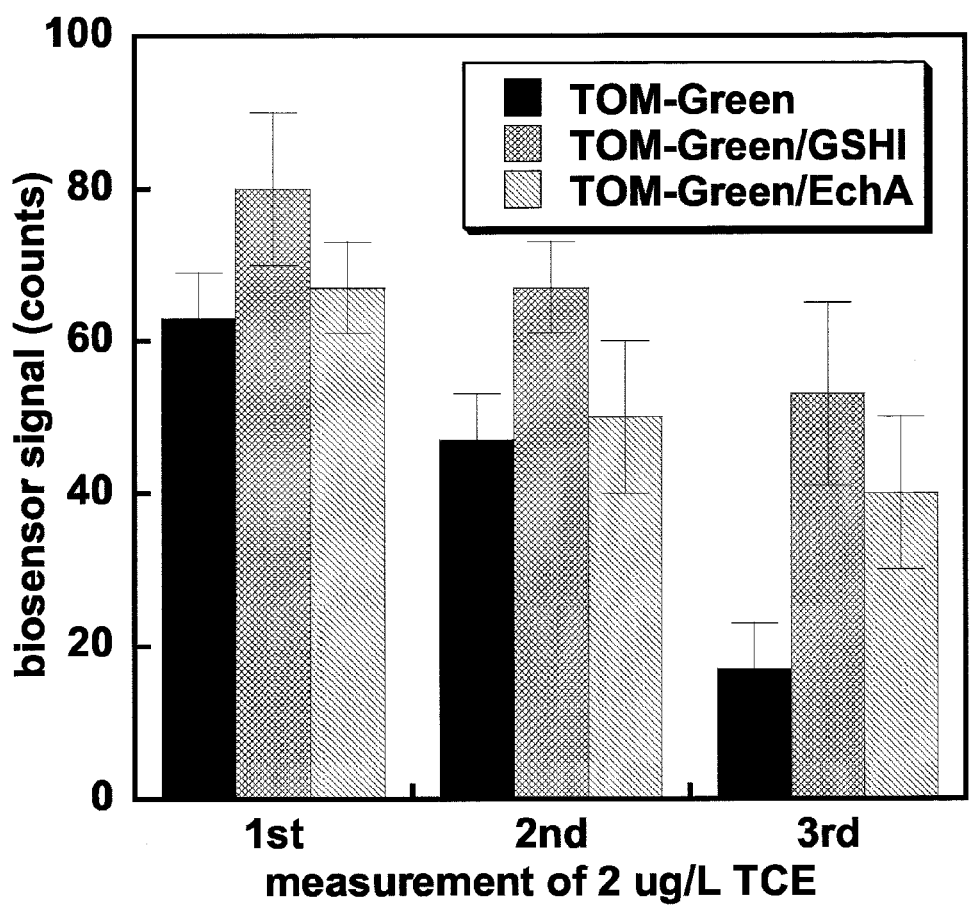
FIG. 5. Signal comparison with all three types of TOM-Green biosensing systems at 2 μg/L TCE.
Figure 10:
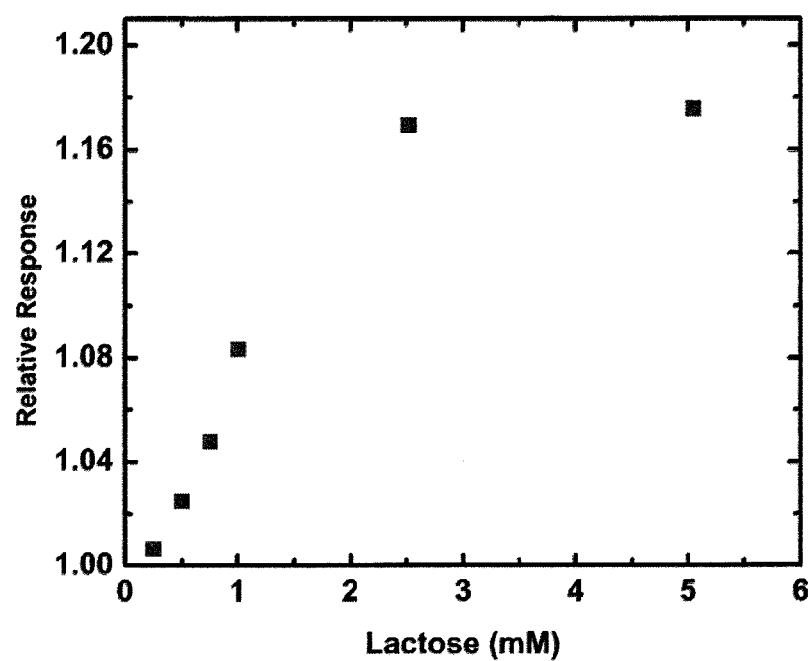
FIG. 10. Response curve for biosensing system A. Biosensing system A is a lactose biosensing system with a thin film of enzyme immobilized on the surface.

The response of biosensing system A to a series of lactose standards is show in FIG. 5. From FIG. 10 it is seen that the biosensing system response begins to saturate at concentrations above 1.01 mM lactose. Signal saturation is due to the presence of analyte at concentrations that exceed the $K_M$ of the enzyme.

Figure 11:
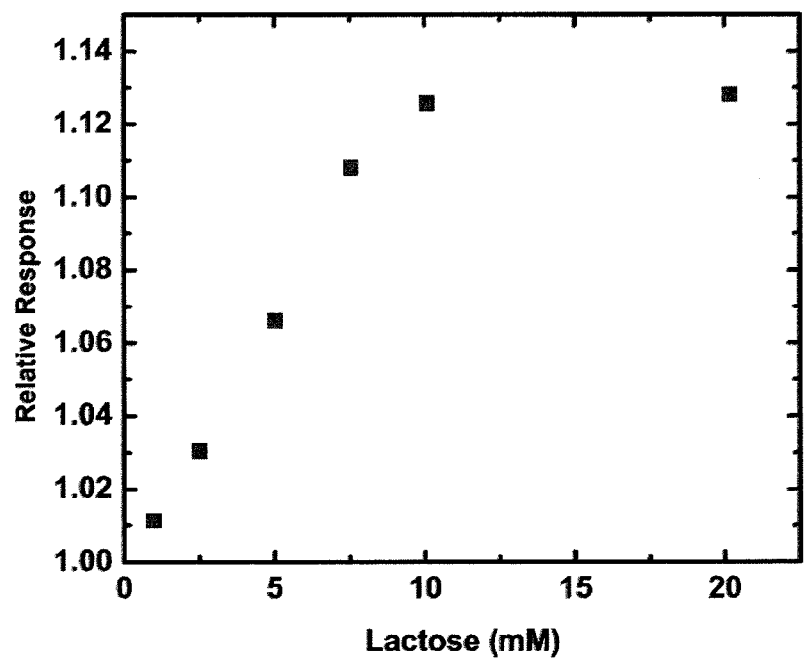
FIG. 11. Response curve for biosensing system B. Biosensor system B is a lactose biosensing system with a porous diffusive barrier.

Biosensing system B has the addition of a diffusive barrier on top of the enzyme layer. This diffusive barrier extended the linear range of biosensing system B into higher concentration ranges, see FIG. 11. For biosensing system B, a porous polycarbonate membrane was immobilized on top of the enzyme layer to act as barrier to analyte mass transfer, which resulted in a lower analyte concentration in the enzyme layer compared to that in bulk solution.

Figure 12:
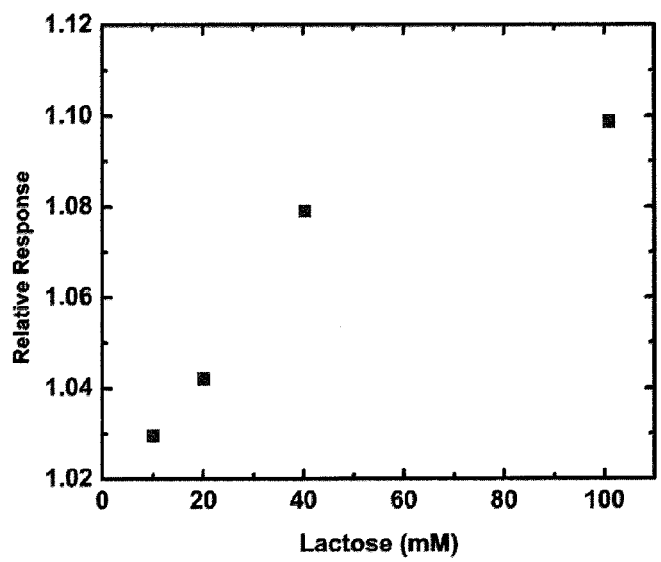
FIG. 12. Response curve for biosensing system C. Biosensing system C is a lactose biosensing system having a less porous diffusive barrier compared to the porous diffusive barrier used in biosensing system B.

Biosensing system C used a less porous polycarbonate membrane relative to the membrane of biosensing system B. This decrease in the porosity of the diffusive barrier resulted in the ability to measure lactose at even higher concentrations relative to biosensing system B, see FIG. 12. The linear range of biosensing system C was extended into this higher concentration regime as a direct result of the increased mass transfer resistance of the less porous diffusive barrier.

Figure 13:
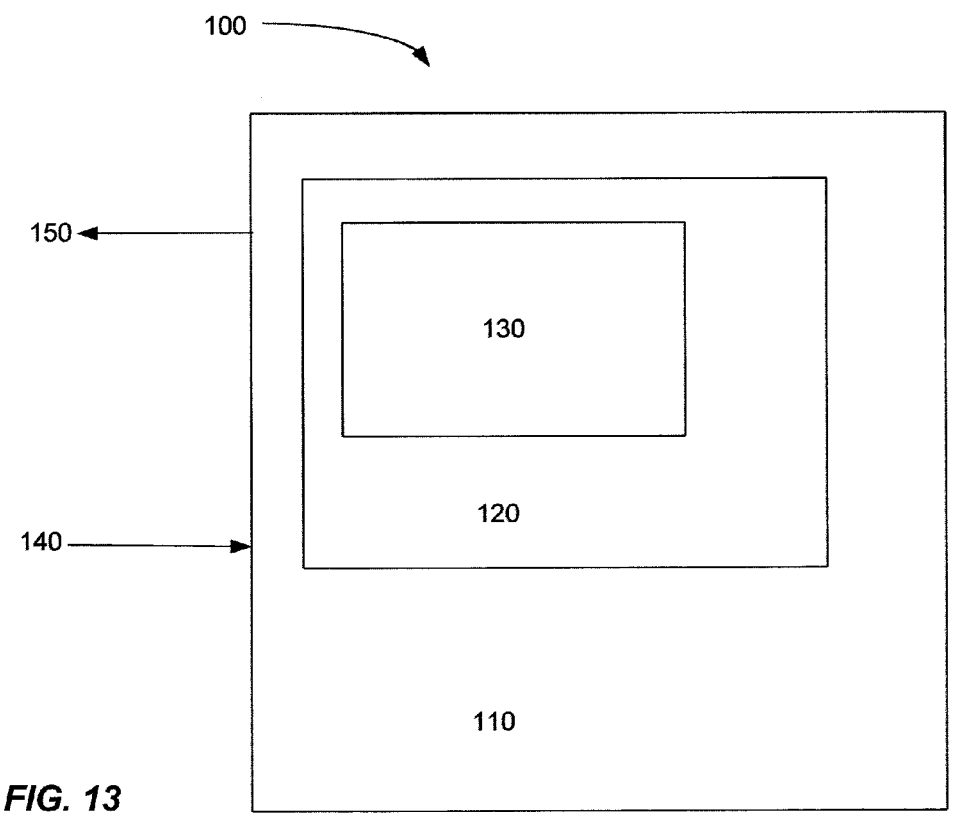
FIG. 13. System for providing design parameters used for constructing biosensing elements.

FIG. 13 shows one exemplary embodiment of a system 100 that is used to provide the appropriate design parameters for constructing biosensing elements used in biosensing systems that have a linear response in a given range of an analyte concentration in a solution. System 100 uses a computer 110 that has a microprocessor 120 that contains software 130 that processes input data 140 to provide output data 150 that contains the appropriate design parameters used for constructing biosensing elements used in biosensing systems that have a linear response in a given range of an analyte concentration in a solution. Output data 150 is displayed upon a screen or saved in a memory storage device or may be transmitted to another memory device or display device.

Constructing the Biosensing System and/or Biosensing Element

In an embodiment, the biosensing element is constructed by putting an immobilized biocomponent within a matrix and coupling that biocomponent-containing matrix onto a transducer. In another embodiment, a biosensing system is created by bonding, affixing or otherwise causing the biocomponent to be in contact with an optode.

Figure 14:
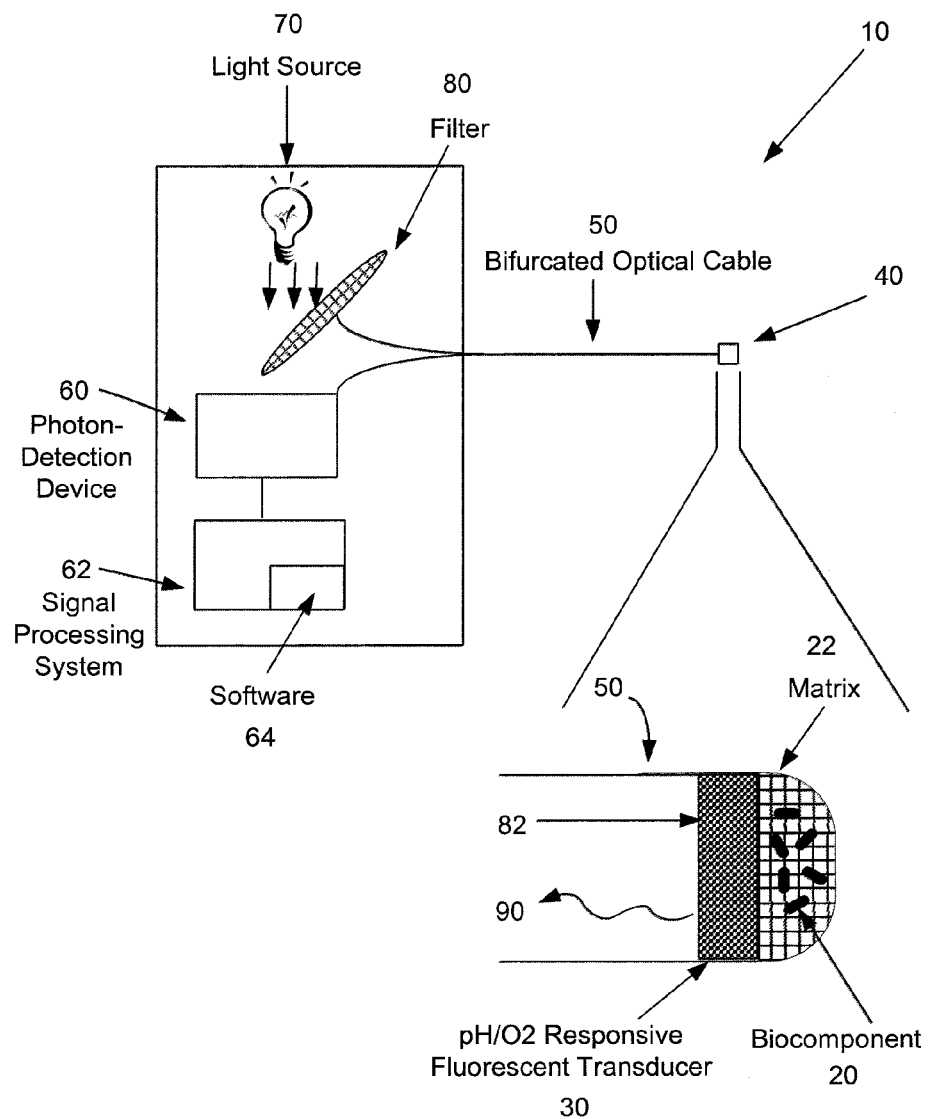
FIG. 14. Schematic representation of a biosensing system.

An embodiment of biosensing system of the present disclosure is depicted in FIG. 14. FIG. 14 depicts a biosensing system 10. Biosensing system 10 includes a biocomponent 20 that is displaced within a matrix 22. Matrix 22 is in direct contact with a transducer 30. Transducer 30 is in direct contact with an end of a bifurcated optical cable 50. Biocomponent 20 and transducer 30 comprise a biosensing element 40. Bifurcated optical cable 50 transmits light from a light source 70 through a filter 80. The light that is transmitted through filter 80 is transmitted through bifurcated optical cable 50 at a first light wavelength 82. Transducer 30 interacts with first light wavelength 82 and luminesces at a second light wavelength 90. Second light wavelength 90 is transmitted through bifurcated optical cable 50 and is detected by a photon-detection device 60 that produces a signal that is sent to a signal processing system 62. Signal processing system 62 contains software 64 that uses an algorithm for determining the concentration of an analyte in a solution based on the luminescence of transducer 30 at second wavelength 90.

Method of Using the Biosensing System and/or Biosensing Element

Figure 15:
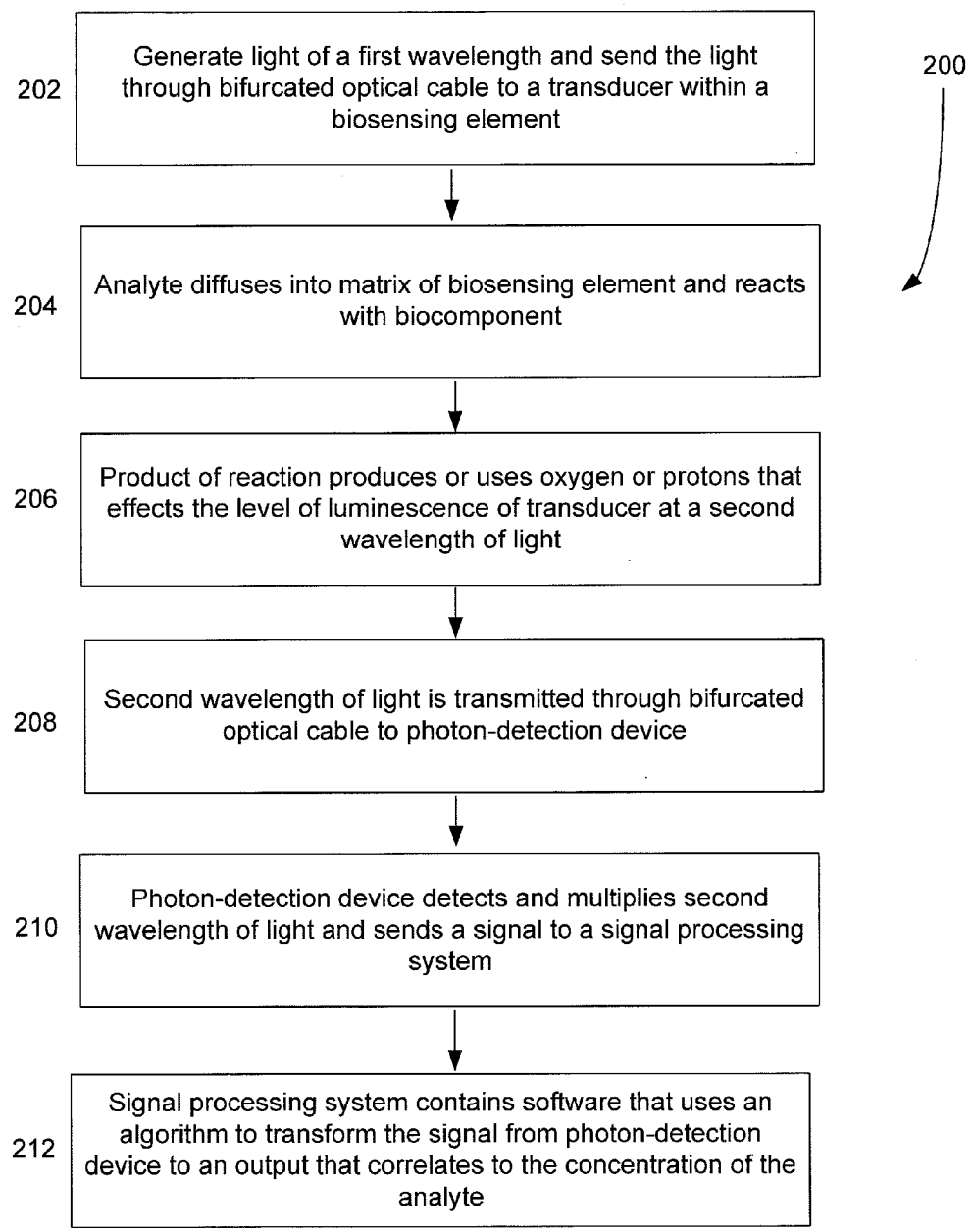
FIG. 15. Schematic representation of exemplary method for using a biosensing system to measure the concentration of an analyte in a solution.

FIG. 15 shows one exemplary method 200 for using a biosensing system to measure the concentration of an analyte in a solution. In step 202, method 200 is implemented by generating light of a first wavelength 82 by light source 70 as it passes through filter 80 and travels down bifurcated optical cable 50 to interact with transducer 30 of biosensing element 40. In step 204, method 200 is further implemented by placing biosensing element 40 at the end of a bifurcated optical cable 50 into a solution. In step 206, an analyte diffuses into matrix 22 and catalyzes the reaction of biocomponent 20. In step 208, the product of the reaction of the analyte with biocomponent 20 produces or uses oxygen and/or hydrogen ions that interact with transducer 30 to affect the amount of fluorescence at a second light wavelength 90 of transducer 30. In step 210, the second light wavelength 90 is transmitted through bifurcated optical cable 50 and detected by photon-detection device 60. In step 212, photon-detection device 60 detects and multiplies the signal of second light wavelength 90 and sends a signal to signal processing system 62. In step 214, signal processing system 62 has software 64 that uses an algorithm that transforms the signal from photon-detection device 60 into an output that can be read as a numerical representation of the concentration of the analyte in the solution that biosensing element 40 was placed into in step 204.

TOM-Green Biosensing Element

Presented herein is a fiber optic enzymatic biosensing system for the fast and simple measurement of TCE concentration and/or the concentration of other halogenated alkenes. In an embodiment of the present disclosure, biosensing systems use TOM as a biocomponent. In another embodiment, oxygenases that use other halogenated alkenes as a substrate may be used as a biocomponent.

TOM is an enzyme involved in the ortho-hydroxylation of toluene and is a member of EC group 1.13. TOM can catalyze the first steps in aerobic TCE dehalogenation with oxygen and reduced nicotinamide adenine dinucloetide (NADH). In these first steps of aerobic TCE dehalogenation, a very active TCE epoxide intermediate is formed. The epoxide formed during the course of the reaction often leads to the inactivation of TOM. In an embodiment of the present disclosure, other enzymes are used to degrade the TCE epoxide into less reactive species thereby preventing the inactivation of TOM by the TCE epoxide and prolonging the useful life of the biosensing elements of the biosensing systems.

In one embodiment, biosensing systems of the present disclosure use a variant of TOM, TOM-Green, as the biocomponent. TOM-Green was created through using a DNA shuffling technique. In one embodiment, TOM-Green is created by making a V106A substitution in the hydroxylase alpha-subunit of TOM from *Burkholderia cepacia* G4. TOM-Green has an initial TCE degradation rate that is twice that of native TOM. In an embodiment, TCE measurement with this biosensing system is performed on the basis of the measurement of oxygen consumption during the oxidation reaction.

In an embodiment of the present disclosure, calcium alginate gel may be used to immobilize whole cells containing TOM-Green on a fiber optic oxygen sensor such as an oxygen optode. The oxygen optode is based on a phosphorescent indicator chemical that exhibits reduced light emission intensity by molecular oxygen via dynamic quenching. One example of an indicator chemical that exhibits reduced light emission intensity by molecular oxygen via dynamic quenching is RuDPP although other chemicals that fluoresce or phosphoresce and whose fluorescence or phosphorescence are quenched by molecular oxygen may be used as well. Other forms of oxygen-interacting fluorophores and oxygen optode technologies may also be used in the biosensing systems of the present disclosure, for example, oxygen-interacting fluorophone containing systems that measure changes in the fluorescence lifetime of a fluorophore. As a result of the enzymatic reaction, the oxygen concentration within the alginate layer decreases with the presence of TCE, which is often apparent as an increase in phosphorescence detection. TCE epoxide toxicity may be evaluated by using two types of *Escherichia coli* cells with the same TOM-Green expressing plasmid but different secondary plasmids, each with a unique epoxide toxicity mitigation mechanism.

Demonstration of the TOM-Green Biosensing System for TCE Measurement

A 0.1 mL aliquot of 25 mg/L aqueous TCE solution was injected into 4.0 mL of measurement solution in which the biosensing element of the biosensing system was immersed. The proposed detection mechanism is that the reaction between TCE and oxygen is catalyzed by the intracellular TOM-Green enzyme immobilized on the biosensing element, and that this reaction consumes oxygen in the solution (as well as NADH inside the cells). As a result, the decrease of oxygen in the alginate layer then causes an increase in the phosphorescence intensity of the immobilized RuDPP because of reduced quenching by oxygen. The biosensing system reading is defined as the measured phosphorescence intensity at a single condition (e.g., measurement solution without analyte at 1 mg/L dissolved oxygen), while the difference between the readings before and after TCE added is termed the biosensing element or biosensing system signal.

The signal of a biosensing system with whole cells of *E. coli* TG1 pBS(Kan)TOM-Green was 2000 counts with a response time of 4 h (FIG. 1), as the result of TCE concentration increase from zero to 0.61 mg/L. When the biosensing system reading reached a steady value (variation less than or equal to the system noise), the remaining TCE concentration in the vial was found to be 0.60±0.03 mg/L by GC-MS. This indicates that TCE detection inside the biosensing system is based on a steady-balance between diffusion and reaction of TCE and oxygen in the biosensing element region, rather than the depletion of TCE in the sample.

Figure 16:
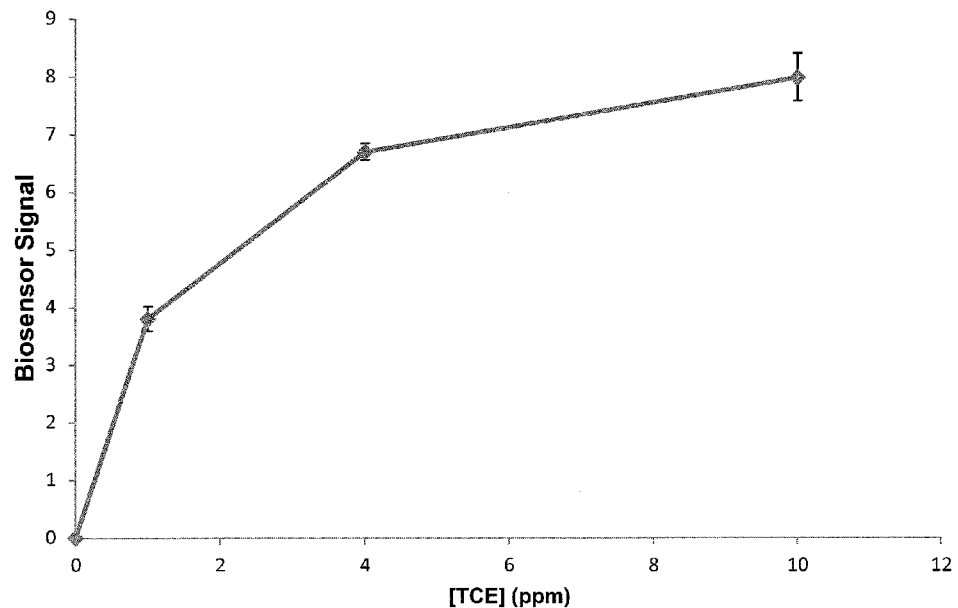
FIG. 16. Response to trichloroethene of a biosensing system with TOM Green enzyme expressed in *E. coli* TG-1 cells immobilized on a pH optode using calcium alginate.

In one example, a TOM-Green biosensing system was constructed using *E. coli* TG-1 cells engineered to express TOM-Green enzyme that were immobilized on a pH optode using calcium alginate, see FIG. 16.

Characterization of TOM-Green Biosensing System
Reproducibility

Biosensing systems were tested with 5 μg/L TCE solutions in order to evaluate reproducibility. The biosensing system signal reproducibility had a relative standard deviation (RSD)=12.8% for n=9, within a batch. In addition, biosensing elements made in different batches were also tested under the same conditions to evaluate batch-to-batch reproducibility. The results showed that these biosensing systems were also consistent with a 11% RSD for biosensing elements made from five different batches.

Effects of Cell Concentration

*E. coli* TG1 pBS(Kan) TOM-Green cells were immobilized at different concentrations in calcium alginate to validate the effect of enzyme concentration on biosensing system performance. Triplicate measurements were made for each of three different cell-to-alginate w/w ratios (3:1, 2:1, and 1:1). All of these biosensing elements were tested with 5 to 20 μg/L TCE and no significant differences in the signal were observed (p<0.01). This result indicates that the oxygen concentration gradient from the alginate layer to the bulk solution is unaffected by cell concentration in the range studied.

Similarly, the biosensing system response time was not dependent upon the cell concentration on the biosensing element. In an embodiment, the measurements with a TCE-based biosensing element require about 2 h each.

Calibration Curve and Limit of Detection

Figure 2:
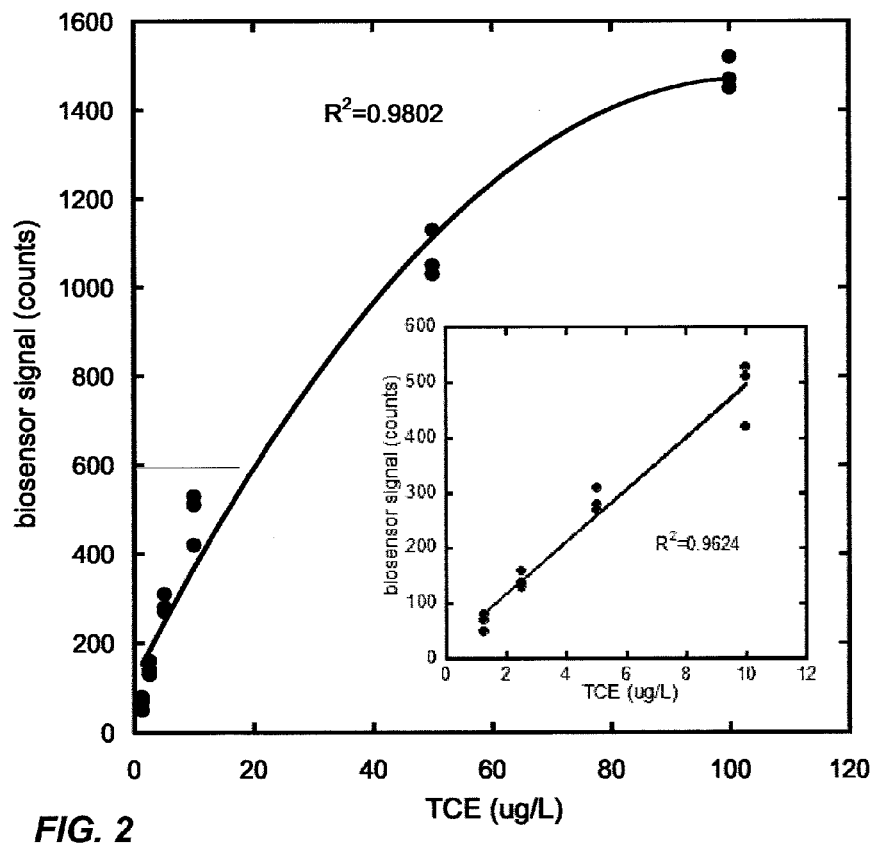
FIG. 2. TOM biosensing system signal as a function of toluene concentration. Inset: biosensing system signals in the low range of toluene concentrations (0-12 μg/L).

A series of TCE solutions from 50 μg/L to 4 mg/L were measured with TOM-Green biosensing systems. Each biosensing element was used only once, and each concentration point was measured in triplicate. The biosensing system signal increased monotonically with TCE concentration and the overall calibration curve was nonlinear over this range. A linear region was observed from 1.2 to 9.8 μg/L TCE with $R^2$=0.962 (FIG. 2). The limit of detection (LOD), calculated as three times the standard deviation of the noise obtained from control experiments, was equal to 1.2 μg/L, less than the EPA Maximum Contaminant Level Goal for TCE (5 μg/L) in National Primary Drinking Water Regulations.

The LOD of the TOM-Green biosensing system for TCE is low, having a linear detection range at levels corresponding to environmentally relevant values.

Accuracy

Water samples from two lakes (Horsetooth Reservoir and City Park Lake, Fort Collins, Colo.) were spiked with TCE to quantify the biosensing system performance in real environmental matrices. In each case, three different TCE concentrations were used, chosen to span the linear measurement range of the biosensing system of this particular embodiment of the present disclosure. The concentrations measured by the TOM-Green biosensing system and the GC/MS method are compared in Table 1, shown below. The average difference between the biosensing system and GC/MS measurements was 0.1±0.2 μg/L with a confidence interval (CI) of 95%, n=18, indicating that the TOM-Green biosensing systems provide accurate and reliable measurement for TCE in these aqueous matrices.

TABLE 1

Comparison of TCE measurements in spiked water samples.

| Sample | TCE concentration (μg/L) | |
|---|---|---|
| | TOM-Green Biosensing System | GC-MS |
| Spiked in Horsetooth Reservoir water | | |
| High | 9.8 ± 0.2 | 9.8 ± 0.1 |
| Medium | 4.9 ± 0.1 | 4.8 ± 0.1 |
| Low | 1.1 ± 0.1 | 1.2 ± 0.1 |
| Spiked in City Park Lake water | | |
| High | 9.8 ± 0.1 | 9.7 ± 0.1 |
| Medium | 4.8 ± 0.1 | 4.8 ± 0.1 |
| Low | 0.8 ± 0.2 | 1.2 ± 0.1 |

Selectivity

TOM-Green has been reported to catalyze the reaction of several chlorinated and aromatic chemicals in addition to TCE via a similar hydroxylation mechanism. Therefore, toluene, benzene, and TCE were chosen to evaluate the selectivity of the TOM-Green biosensing system. All of these analytes were measured at a concentration of 1 mg/L. The biosensing system signal was largest for TCE (2280±80 counts), followed by toluene (570±60 counts), and then benzene (40±10 counts). This trend is consistent with data from a previous study in which TOM-Green was found to have a higher degradation rate for TCE than for other analytes. The 1 mg/L TCE concentration registered the highest biosensing system signal, suggesting that the signal increases monotonically when TCE concentration increases.

Effects of Temperature and pH on Biosensing System Signal

Hydrogen ion concentration, as measured by pH, and temperature are two crucial factors in environmental monitoring, since both enzyme activity and mass transfer rates of TCE and oxygen could be affected. In addition, the phosphorescence properties of RuDPP are also temperature dependent. To quantify the effect of pH on the TOM-based biosensing system signal, sets of three biosensing systems were tested in measurement solutions buffered at pH 5.0, 6.0, or 7.0, spanning a common pH range in typical groundwater aquifer. The signals corresponding to 5 μg/L TCE at different pH values were 290±20 counts (pH=5), 280±30 counts (pH=6), and 300±40 (pH=7), indicating that the measurements of the TOM-based biosensing system were independent of pH in this range. Similarly, the signals of a set of three biosensing systems at three temperatures were investigated. The signals of these biosensing systems to 5 μg/L TCE were 270±50 counts at 15° C., 290±20 counts at 20° C. and 430±30 counts at 30° C.

Activity Retention

Figure 3:
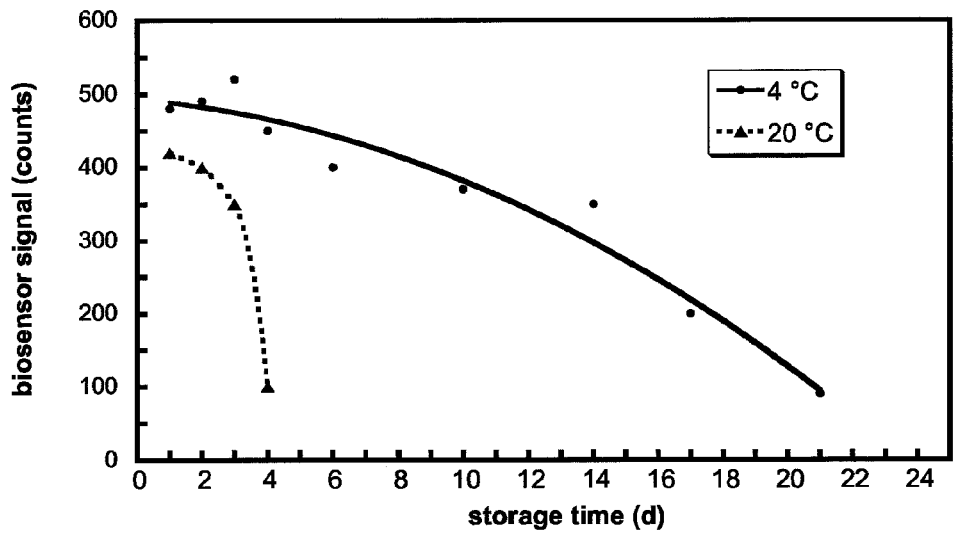
FIG. 3. Activity retention of TOM-Green biosensing elements stored at two temperatures in measurement solution (without formate); each point represents the reading for a 92 μM toluene solution.

Biosensing systems of the present disclosure retain activity with use or storage or prolonged periods of time and through multiple uses. To investigate the retention of activity among biosensing systems, two groups of biosensing elements were stored in a measurement solution without TCE at 4° C. or 20° C. At various intervals, biosensing elements were transferred from the storage solution and used to measure 10 μg/L TCE. For both storage temperatures, the biosensing system performance declined over time, and eventually no detection of TCE was recorded. Biosensing elements stored at 4° C. retained activity over a longer period than those stored at 20° C. (FIG. 3). Thus, NADH starvation or enzyme denaturation may be responsible for the deteriorating biosensing system activity over time, especially at higher temperature.

In one embodiment of the present disclosure, NADH may be regenerated within a biocomponent cell through a coenzyme system. In another embodiment, NADH may be made available to the biocomponent via capillary action or pumping of a delivery tube.

In one embodiment, the retention of activity of TOM is increased through the regeneration of NADH. NADH regeneration via an external supply of formate can partially replenish biocomponent TOM activity since intracellular formate dehydrogenase can reduce the NAD+ to NADH by the oxidation of formate. NADH regeneration can also be accomplished by providing formate dehydrogenase as an additional biocomponent on the same biosensing element or on a different biosensing element that is part of the same biosensing system; and supplying formate to the formate dehydrogenase in order to regenerate the supply of NADH and/or NADPH. Regeneration experiments were conducted to test the extent of regeneration via this formate scheme using TOM-Green biosensing systems.

Figure 6:
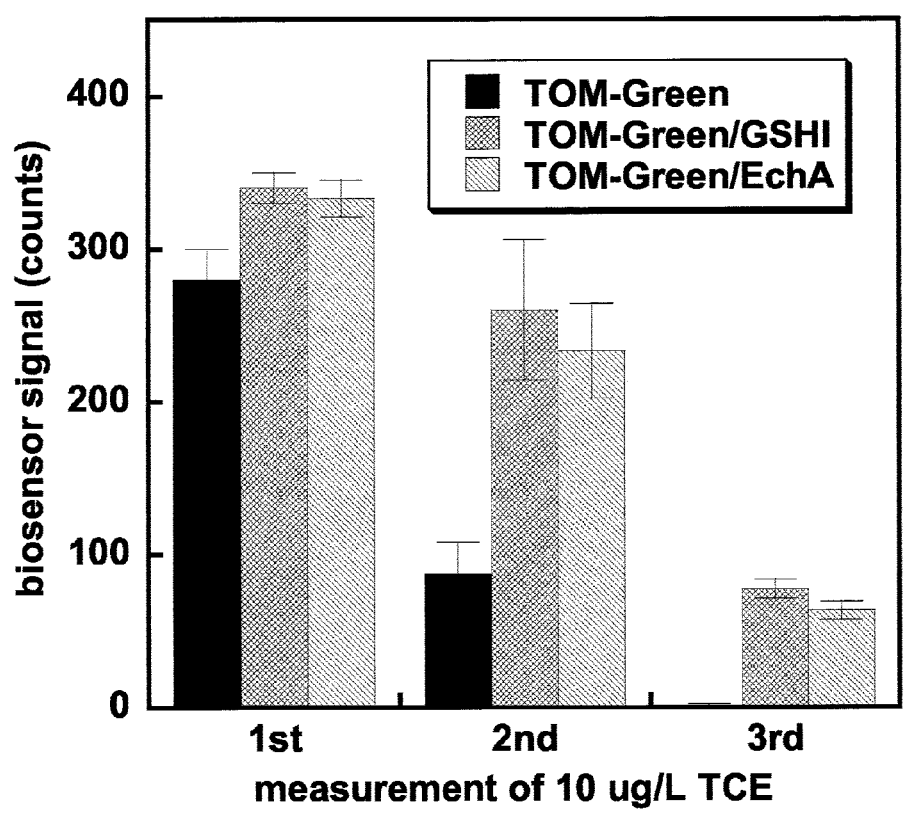
FIG. 6. Signal comparison with all three types of TOM-Green biosensing systems at 10 μg/L TCE.
Figure 7:
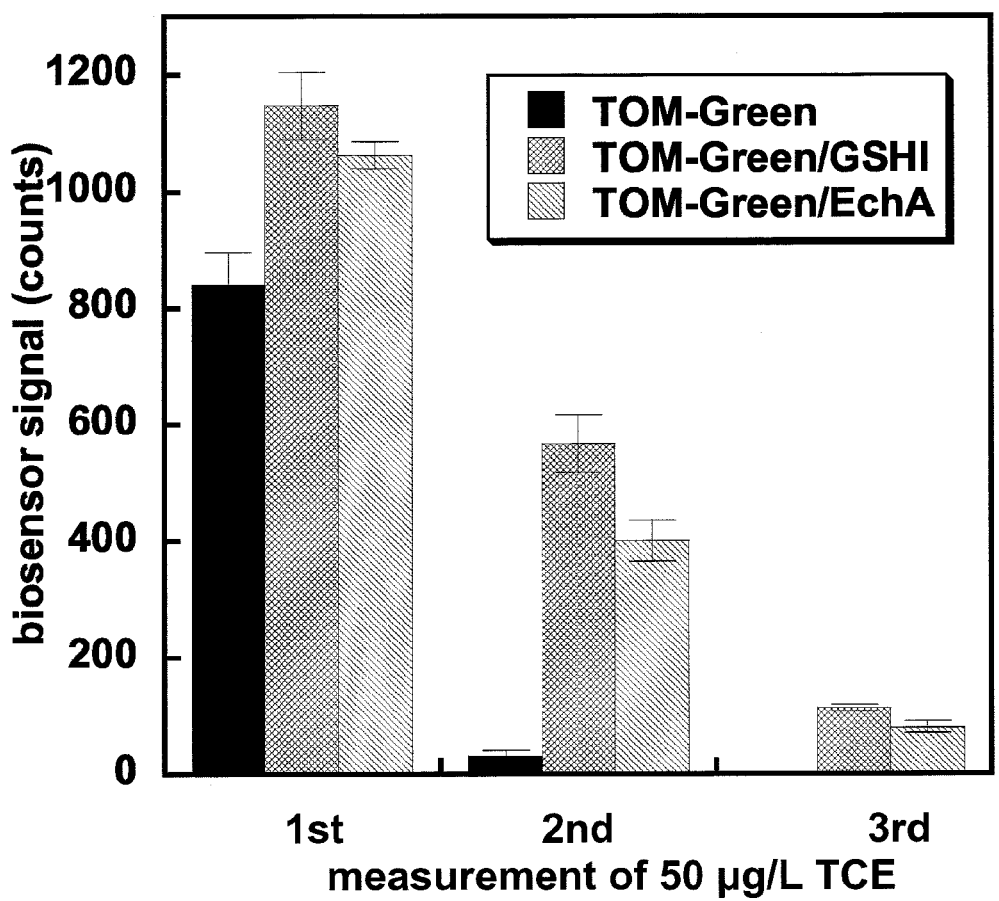
FIG. 7. Signal comparison with all three types of TOM-Green biosensing systems at 50 μg/L TCE.

In comparison with controls having no formate regeneration between repeated measurements, the signal from regenerated TOM-Green biosensing elements showed 2±3% increase at a TCE concentration of 50 μg/L, 2±4% increase at a TCE concentration of 10 μg/L and 5±5% increase at a TCE concentration of 2 μg/L, indicating that NADH regeneration has a smaller effect than TCE epoxide on the biocomponent cells, see FIGS. 5-7.

Mitigation of TCE Epoxide Toxicity

In one embodiment, biosensing systems disclosed herein contains at least two biocomponents, at least a first biocomponent that react directly or indirectly with an analyte of interest and at least a second biocomponent that mitigages the damage caused by the product or by-product of the reaction catalyzed by the first biocomponent. Damage caused by the product or by-product of the reaction can be mitigated by enzymes including epoxide hydrolase, glutathione synthetase, glutathione S-transferase and gamma-glutamylcysteine synthetase or other enzymes that quench or otherwise react with products or by-products of biocomponent reactions.

In another embodiment, biosensing systems disclosed herein contain at least a first biocomponent that reacts directly or indirectly with an analyte of interest.

TCE epoxide is electrophilic and may directly or indirectly react with various intracellular biological molecules such as DNA, RNA, lipids, proteins, and other small molecules. The reactions often result in the inactivation of enzymes, cells or other biocomponents. $E.\ coli$ cells with TOM-Green plasmid and gamma-glutamylcysteine synthetase (GSHI), EC number 6.3.2.2, and/or epoxide hydrolase (EchA), EC numbers 3.3.2, 3.3.2.3, 3.3.2.9, 3.3.2.10, plasmids were developed to mitigate the damage created by TCE epoxide.

Biosensing systems were made with $E.\ coli$ TOM-Green, $E.\ coli$ TOM-Green/GSHI, and $E.\ coli$ TOM-Green/EchA. Biosensing systems in each group were made in a single batch and tested with 50 μg/L TCE ("high" concentration), 10 μg/L TCE ("medium" concentration), and 2 μg/L TCE ("low" concentration), in triplicate, while each biosensing system was tested three times at the same TCE concentration. At high TCE concentration, the $E.\ coli$ TOM-Green biosensing system was inactivated after the first use, while the second measurement of $E.\ coli$ TOM-Green/GSHI and $E.\ coli$ TOM-Green/EchA biosensing systems retained about 50% of their initial signals, and the third measurement had about 10% of the initial signals, see FIG. 4. At a medium TCE concentration range, the second measurement signals were about 75-80% that of first measurement in the case of the TOM-Green/GSHI and TOM-Green/EchA biosensing systems, while the TOM-Green biosensing systems retained about 30% activity after the first use. In the low concentration range, the TCE toxicity effect was less obvious since all three kinds of biosensing systems shared the same range of activity retention after first time usages. The TOM-Green/GSHI had a higher biosensing system signal than TOM-EchA in all conditions.

Demonstration of the Toluene Dioxygenase Biosensing System for TCE Measurement

Figure 17:
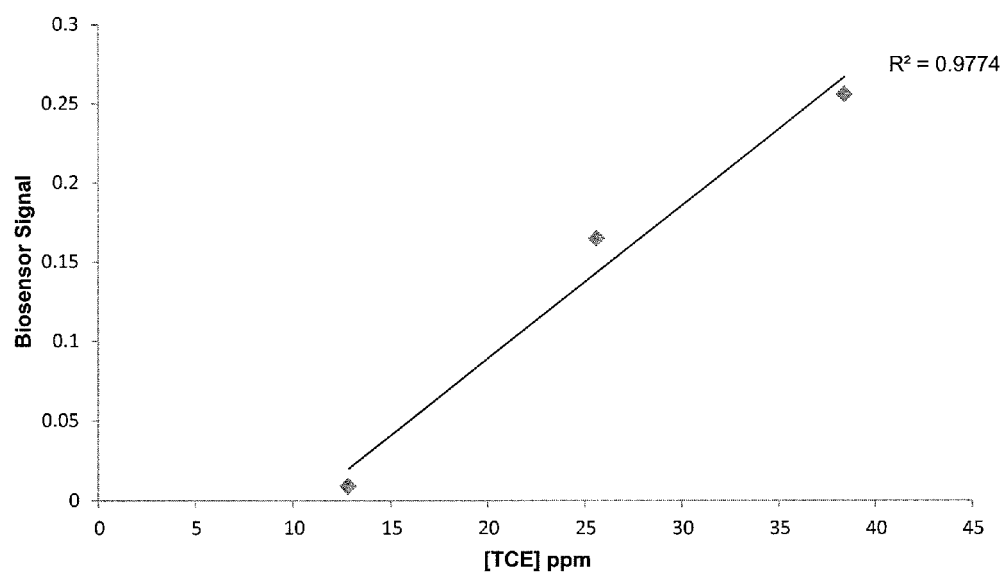
FIG. 17. Response to trichloroethene of a biosensing system with toluene dioxygenase in *Pseudomonas putida* F1 with an oxygen optode transducer.

In one embodiment, a biosensing system having toluene dioxygenase in $Pseudomonas\ putida$ F1 as a biocomponent and an oxygen optode transducer was used to measure the concentration of TCE, see FIG. 17.

In another embodiment, a biosensing system may be constructed using substantially purified toluene dioxygenase as a biocomponent.

EXAMPLES

Bacterial Strains and Growth Conditions

The various biocomponent enzymes of the biosensing systems, TOM-Green, TOM-Green/EchA, and TOM-Green/GSHI were expressed in $E.\ coli$ strain TG1. $E.\ coli$ cultures were grown aerobically on agar plates made from Luria-Bertani (LB) medium with 20 g/L Bacto-agar (Difco) and 100 mg/L kanamycin (plus 50 mg/L chloramphenicol in the case of TOM-Green/EchA and TOM-Green/GSHI) at 30° C. for 24 h. A culture tube containing 2 mL LB medium supplemented with same concentrations of antibiotics was inoculated from an individual colony on an agar plate and shaken overnight at 30° C. and 200 rpm, then transferred to a flask containing 200 mL of the same LB-Kan medium and shaken at 30° C. and 200 rpm. The cell concentration was measured as culture absorbance at 600 nm (optical density at 600 nm, $OD_{600}$) with a spectrophotometer Spectronic® 20 Genesys™, Thermo Electron Corporation. IPTG solution was prepared with deionized water and added to the culture with a final concentration of 1 mM in the early exponential growth phase (OD600 of 0.6) to induce TOM-Green, TOM-Green/EchA and TOM-Green/GSHI expression. The culture was harvested 4 h after IPTG was added, centrifuged, and resuspended in 20 mL of a solution containing 10 mM phosphate-buffered saline at pH 7.4 and stored at 4° C. until further use.

Exemplary Biosensing Element

A biosensing element consisting of a layer of whole cells immobilized over an oxygen optode was constructed from a 25-cm section of polymethylmethacrylate (PMMA) optical fiber terminated with a straight tip (ST) connector. The fiber jacket was detached from 1 mm of the distal end (non-connector terminated) and then polished with 2000-grit and 3 μm polishing film (part of a fiber optic tool kit, IF-TK4-RP2, Industrial Fiber Optics) to minimize potential signal loss due to scattering. One mg of the oxygen-sensitive RuDPP was dissolved into 1 mL chloroform and mixed with 200 mg silicone gel (clear RTV silicone, Permatex, Inc.). A 1 μL aliquot of this mixture was then added to the polished fiber tip. The RuDPP gel layer was affixed to the optical fiber end as soon as the chloroform evaporated. Previously stored E. coli whole cells containing plasmids encoding enzymes such as TOM, TOM-Green, epoxide hydrolase, glutathione synthetase, glutathione S-transferase, and/or gamma-glutamylcysteine synthetase, were centrifuged and mixed with sodium alginate solution (2.5% w/w) in a cell-to-alginate ratio (wet cell mass:alginate solution) of 1:1 w/w. A 2-μL aliquot of the cell-alginate mixture was placed on the tip of each oxygen optode and immobilized after immersing the optode in 0.47 M calcium chloride solution for 30 min at 0° C. All biosensing elements were stored at 0° C. in a solution of 0.15 M NaCl and 0.025 M $CaCl_2$ at pH 7.0, the "measurement solution".

Biosensing System Measurement Protocols

In one embodiment, biosensing system experiments were performed in 5 mL glass vials containing 4 mL of measurement solution saturated with air at room temperature with a small magnetic stir bar for rapid mixing. The biosensing element was immersed in this solution, sealed in the glass vial with a rubber septum, and shielded from external light sources. Aliquots of 0.1 mL of a TCE solution of 0.1 to 4 mg/L were injected into the measurement solution after the sensor had produced a steady output. A steady output is defined as the time when the variation in the output was no larger than the peak-to-peak noise for a period of at least 5 min.

In another embodiment, biosensing systems may be used for continuous measurements.

TCE Concentration Measurement by Gas Chromatography

To assess the accuracy of the TCE concentration data obtained from the biosensing systems, GC analysis was performed via a modification of EPA Method 8260b. After a biosensing system measurement, 0.75 mL of aqueous solution was collected from the measurement vial and transferred into a 2 mL glass screw-top GC vial containing 0.75 mL of chloroform. The GC vial was then capped with a Teflon-coated septum and mixed on a rotating wheel for 15 min. One μL of the chloroform phase was injected into a Hewlett Packard 5890 gas chromatograph equipped with a HP model 5971A mass spectrometric (MS) detector. A calibration curve of the GC-MS total ion count peak area vs. the TCE concentration in solution was obtained using dilutions of the 200 mg/L TCE standard solution. The GC calibration curve was linear over the range of TCE concentrations from 1 to 1000 μg/L ($R^2$=0.973).

Preparation of Biosensing Element Using Dry-Heated Cells

In order to prepare dry heated cells, cells stored at 4° C. in phosphate-buffered saline solution were centrifuged at 15,000×g for 3 minutes and were washed twice with distilled water. These cells were suspended in a small quantity of water (3 mL of stored cell suspension were washed and then suspended in 0.5 mL of water). This suspension was put in a 10-mL beaker and water was completely removed by vacuum drying at 35° C. It took about an hour to dry these cells. The dried cells were then scratched off from the surface of beaker using a spatula. The beaker was then covered with aluminum foil and left in the oven at a constant temperature of 270° C. and for a given period of time (30 sec, 60 sec, etc.). These dry heated cells looked like a highly porous solid and had a light orange color. These dry-heated cells (~0.003-0.004 g) were also immobilized using the same entrapment method. However it was found that when these cells were directly mixed with 4% (w/v) of alginate, there were a lot of small bubbles in the cell-alginate mixture. Since it was important to eliminate these bubbles in order to obtain a stable response, these cells were first suspended in 10 μL of NaOH (pH 7.0) in a 1.5 mL-vial and then 8% (w/v) of alginate was added to it (from about 0.3 to about 0.5 g/g of dry wt. of cells to wt. of alginate). This mixture was used to make the biosensing element.

Preparation of Biosensing Element Using Chloramphenicol-Treated Cells

Cells stored at 4° C. in phosphate-buffered saline were centrifuged at 15,000×g for 2 minutes and the pellet was then washed twice with saline (9 g/L of NaCl [pH 7.1]) containing 50 μg/mL of chloramphenicol. Next, sodium alginate (4% w/v in water) containing either 50 or 200 μg/mL of chloramphenicol was added and mixed well with the cell pellet. This cell and alginate mixture was kept for 5 minutes at room temperature before it was used to make the biosensing element.

Preparation of Biosensing Element Using Protease Inhibitor Treated Cells

Cells stored at 4° C. in phosphate-buffered saline were centrifuged at 15,000×g for 2 minutes and the pellet was then washed twice with saline (9 g/L of NaCl [pH 7.1]) containing 5 μL of protease inhibitor cocktail in 1 mL of saline solution. This cocktail was prepared by adding 215 mg of lyophilized protease inhibitor in a solution containing 1 mL of DMSO (Dimethyl sulfoxide) and 4 mL of deionized water. The cocktail had a broad specificity for the inhibition of serine, cysteine, aspartic and metalloproteases, and aminopeptidases. It was stored at −20° C. in the freezer. These cells were then mixed with Na-alginate solution (4% w/v) containing 200 μL of cocktail per mL of alginate solution. The cell-alginate mixture was left for about 5 minutes at room temperature before it was used for making the biosensing element. The ratio of the weight of wet cells to the weight of alginate used in the experiment was 0.72 g/g.

Preparation of Biosensing Element with a Poly-L-Lysine Coating

The alginate bead was coated with poly-L-lysine (PLL) by preparing the biosensing element with a biocomponent as described above. The Ca-alginate bead on the biosensing element was then washed twice with saline solution (9 g/L of NaCl in water). Then the biosensing element was immersed in 10 mL of 0.4% (w/v) of poly-L-lysine.HCl solution, stored at 4° C. inside the refrigerator) in saline for 30 minutes at 30° C.

Oxygen Sensor Biosensing Element Construction

In one embodiment, the optode used in the biosensing element is an oxygen optode. An oxygen optode is a sensor based on optical measurement of the oxygen concentration. In one embodiment, a chemical film is glued to the tip of an optical cable and the fluorescence properties of this film depend on the oxygen concentration. Fluorescence is at a maximum when there is no oxygen present. When an $O_2$ molecule comes along it collides with the film and this quenches the photoluminescence. In a given oxygen concentration there will be a specific number of $O_2$ molecules colliding with the film at any given time, and the fluorescence properties will be stable.

In one example, a biosensing element for measuring the concentration of oxygen consisted of a layer of immobilized whole cells over an oxygen optode, which was constructed from a 25-cm section of PMMA optical fiber terminated with a straight tip (ST) connector. The fiber jacket was detached from 1 mm of the distal end (non-connector terminated) and then polished with 2000-grit and 3 μm polishing film (part of a fiber optic tool kit, IF-TK4-RP2, Industrial Fiber Optics) to minimize potential signal loss due to scattering. One mg of the oxygen-sensitive phosphorophore RuDPP, which is classified as phosphorophores since its longer decay lifetime than typical fluorophores, was dissolved into 1 mL chloroform and mixed with 200 mg silicone gel (clear RTV silicone, Permatex, Inc.). A 1-μL aliquot of this mixture was then added to the polished fiber tip. The RuDPP gel layer was affixed to the optical fiber end as soon as the chloroform evaporated. Previously stored *E. coli* whole cells (with plasmids which may encode for TOM, TOM-Green, epoxide hydrolase, glutathione synthetase, glutathione S-transferase, and/or gamma-glutamylcysteine synthetase, for example) were centrifuged and mixed with sodium alginate solution (2.5%) in a cell-to-alginate ratio (wet cell mass:alginate solution) of 1:1 w/w unless otherwise specified. 2 μL of the cell-alginate mixture was placed on the tip of each oxygen optode and immobilized after immersing the optode in 0.47 M calcium chloride solution for 30 min at 0° C. All biosensing elements were stored at 0° C. in a measurement solution of 0.15 M NaCl and 0.025 M $CaCl_2$ at pH 7.0.

Oxygen and pH Biosensing System Instrumentation

The oxygen biosensing system instrumentation consisted of two separate optoelectronic modules: a 470-nm LED and a 450/60 nm optical bandpass filter (Chroma Technologies) as the excitation light source, and a computer-controlled Ocean Optics USB4000-FL spectrometer with 10 nm resolution for detection. The 470-nm excitation light was delivered through one leg of a bifurcated optical fiber assembly that has two 1-mm fibers side-by-side in the common end (Ocean Optics, Inc.), which was connected with the biosensing system via an ST connector. The phosphorescent emission light (peak at 620 nm) from the biosensing element was directed back into the detector through the other leg of the bifurcated optical fiber and measured by the spectrometer (sensitivity of approximately 60 photons/count at 600 nm). The spectrometer output from 615 nm to 625 nm was integrated over 200 ms and five such values were averaged to yield one measurement value per second. The change in the intensity of the emission light over time correlates to the oxygen concentration change in the RuDPP layer of the biosensing element. Alternatively, the fluorescence lifetime of a fluorophore, such as RuDPP, may be measured and correlated to an oxygen concentration.

In another embodiment, the fluorescence lifetime of a fluorophore in a pH optode may be measured and correlated to a change in hydrogen ion concentration. Alternatively, a pH optode can measure the change in the intensity of the emission light of a fluorophore, such as fluorescein, over time and correlate that change in intensity to the hydrogen ion concentration and thus to the concentration of an analyte of interest.

The above examples, embodiments, definitions and explanations should not be taken as limiting the full metes and bounds of the invention.

The invention claimed is:

1. A biosensing system that measures the concentration of a halogenated alkene in a solution, said biosensing system comprising:
   a first biocomponent that catalyzes the reaction of said halogenated alkene;
   a second biocomponent that catalyzes the reaction of a halogenated alkene epoxide; and
   a transducer layer that luminesces, wherein said transducer layer is part of an optode;
   wherein said first biocomponent and said second biocomponent comprise cells, and wherein said cells contain enzymes selected from the group consisting of oxygenases, monooxygenases, dioxygenases, toluene dioxygenase, toluene ortho-monooxygenase, toluene ortho-monooxygenase-Green, epoxide hydrolase, glutathione synthetase, glutathione S-transferase and gamma-glutamylcysteine synthetase; and
   wherein said cells of said first biocomponent and said second biocomponent are immobilized within a matrix, said matrix in contact with, and distal to, said transducer layer.

2. The biosensing system of claim 1
   wherein said first biocomponent catalyzes the reaction of said halogenated alkene and oxygen and said halogenated alkene epoxide is created by said first biocomponent catalyzed reaction,
   wherein said transducer layer luminescence is altered by oxygen and/or hydrogen ions in said solution, and
   wherein photons from the luminescence of said transducer layer enter into a fiber optic cable and are transmitted to a photomultiplier, and
   wherein said photomultiplier produces an output signal that is coupled to an algorithm that transforms the signal generated by said photomultiplier into an output correlated to the concentration of said halogenated alkene in the solution.

3. The biosensing system of claim 2 wherein said halogenated alkene is selected from the group consisting of tetrachloroethene, trichloroethene, dichloroethene, and monochloroethene.

4. The biosensing system of claim 2 wherein
   said first biocomponent is selected from the group consisting of toluene orthomonooxygenase and toluene ortho-monooxygenase-Green;
   said second biocomponent is selected from the group consisting of epoxide hydrolase, glutathione synthetase, glutathione S-transferase and gamma-glutamylcysteine synthetase; and
   said transducer layer comprises a luminescent reagent selected from the group consisting of RuDPP and fluorescein.

5. The biosensing system of claim 1, wherein said cells are alive.

6. The biosensing system of claim 1, wherein said cells are dead.

7. The biosensing system of claim 1, wherein the cells comprise genes encoding said enzymes and wherein the nucleotide coding sequences of said genes for said biocomponent enzymes are on a plasmid or plasmids within a whole cell biocomponent or on a chromosome of a whole cell biocomponent.

8. The biosensing system of claim 1, wherein said optode is selected from the group consisting of an oxygen optode and a pH optode.

9. The biosensing system of claim 1, wherein said halogenated alkene is trichloroethene,
   wherein said first biocomponent catalyzes the reaction of trichloroethene and oxygen and said second biocomponent catalyzes the reaction of trichloroethene epoxide, and
   wherein said transducer layer luminescence is altered by oxygen in said solution, and
   wherein photons from the luminescence of said transducer layer enter into a fiber optic cable and are transmitted to a photomultiplier, and
   wherein said photomultiplier produces an output signal that is coupled to an algorithm that transforms the signal generated by said photomultiplier into an output correlated to the concentration of trichloroethene in the solution.

10. The biosensing system of claim 1, wherein said first biocomponent catalyzes the reaction of a halogenated alkene and oxygen and said second biocomponent catalyzes the reaction of a halogenated alkene epoxide created by said first biocomponent catalyzed reaction, and wherein said transducer layer comprises compounds and chemical complexes containing ruthenium, and wherein said transducer layer luminescence is altered by oxygen in said solution, and wherein photons from the luminescence of said transducer layer enter into a fiber optic cable and are transmitted to a photomultiplier, and wherein said photomultiplier produces an output signal that is coupled to an algorithm that transforms the signal generated by said photomultiplier into an output correlated to the concentration of said halogenated alkene in the solution.

11. A biosensing system that measures the concentration of a halogenated alkene in a solution, said biosensing system comprising a first biocomponent that catalyzes the reaction of said halogenated alkenes;

a second biocomponent that catalyzes the reaction of a halogenated alkene epoxide;

a transducer layer that luminesces wherein said transducer layer is part of an optode; and wherein said first biocomponent and said second biocomponent comprise purified cell-free enzymes selected from the group consisting of oxygenases, monooxygenases, dioxygenases, toluene dioxygenase, toluene ortho-monooxygenase, toluene ortho-monooxygenase-Green, epoxide hydrolase, glutathione synthetase, glutathione S-transferase and gamma-glutamylcysteine synthetase;

wherein said purified cell-free enzymes of said first biocomponent and said second biocomponent are immobilized within a matrix, said matrix in contact with, and distal to, said transducer layer.

12. The biosensing system of claim 11, wherein said first biocomponent is toluene ortho-monooxygenase, toluene ortho-monooxygenase-Green, or toluene dioxygenase.

13. The biosensing system of claim 11, wherein said halogenated alkene is trichloroethene.

14. The biosensing system of claim 11, wherein said transducer layer comprises a luminescent reagent that is RuDPP or fluorescein.

* * * * *